United States Patent
Borie et al.

(10) Patent No.: US 9,914,779 B2
(45) Date of Patent: Mar. 13, 2018

(54) ADMINISTRATION OF ALPHA4BETA7 HETERO-DIMER-SPECIFIC ANTIBODY

(71) Applicant: AMGEN INC., Thousand Oaks, CA (US)

(72) Inventors: Dominique Christian Borie, Palo Alto, CA (US); Hailing Hsu, Moorpark, CA (US); Wei-Jian Pan, Pullman, WA (US); William Rees, Seattle, WA (US); Barbara Anne Sullivan, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 391 days.

(21) Appl. No.: 14/360,087

(22) PCT Filed: Nov. 21, 2012

(86) PCT No.: PCT/US2012/066345
§ 371 (c)(1),
(2) Date: May 22, 2014

(87) PCT Pub. No.: WO2013/078375
PCT Pub. Date: May 30, 2013

(65) Prior Publication Data
US 2014/0322209 A1    Oct. 30, 2014

Related U.S. Application Data

(60) Provisional application No. 61/599,221, filed on Feb. 15, 2012, provisional application No. 61/563,430, filed on Nov. 23, 2011.

(51) Int. Cl.
| | | |
|---|---|---|
| *A61K 39/395* | (2006.01) | |
| *C07K 16/18* | (2006.01) | |
| *C07K 16/28* | (2006.01) | |
| *G01N 33/569* | (2006.01) | |
| *A61K 39/00* | (2006.01) | |

(52) U.S. Cl.
CPC ...... *C07K 16/2842* (2013.01); *C07K 16/2839* (2013.01); *G01N 33/56972* (2013.01); *A61K 2039/505* (2013.01); *A61K 2039/54* (2013.01); *A61K 2039/545* (2013.01); *C07K 2317/90* (2013.01); *G01N 2333/70546* (2013.01); *G01N 2800/065* (2013.01); *G01N 2800/52* (2013.01)

(58) Field of Classification Search
None
See application file for complete search history.

(56) References Cited

U.S. PATENT DOCUMENTS

2010/0254975 A1    10/2010  Hsu et al.

FOREIGN PATENT DOCUMENTS

| WO | WO-01/78779 A2 | 10/2001 |
|---|---|---|
| WO | WO-2008/115504 A2 | 9/2008 |
| WO | WO-2009/140684 A2 | 11/2009 |
| WO | WO-2010/107752 A2 | 9/2010 |
| WO | WO-2011/088120 A1 | 7/2011 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Abraham et al., Inflammatory bowel disease, *N Engl J Med.*, 361(21):2066-78 (2009).
Arihiro et al., Differential expression of mucosal addressin cell adhesion molecule-1 (MAdCAM-1) in ulcerative colitis and Crohn's disease, *Pathol Int.*, 52(5-6):367-74 (2002).
Ausubel et al., Current Protocols in Molecular Biology, Greene Publishing Associates, (1992).
Branden et al, Introduction to Protein Structure, Garland Publishing, New York, (1991).
Behm et al. Humanized antibody to the alpha4beta7 integrin for induction of remission in ulcerative colitis. *Cochrane Database Syst Rev.* (1):CD007571 (2009).
Briskin et al., Human mucosal addressin cell adhesion molecule-1 is preferentially expressed in intestinal tract and associated lymphoid tissue, *Am J Pathol.*, 151(1):97-110 (1997).
Creighton, Proteins, Structures and Molecular Principles, Freeman and Company, N.Y. (1984).
Danese et al., Antibody to alpha4beta7 integrin for ulcerative colitis. *N Engl J Med.*, 353(11):1180-1 (2005).
Feagan et al., Treatment of ulcerative colitis with a humanized antibody to the alpha4beta7 integrin. *N Engl J Med.*, 352(24):2499-507 (2005).
Feagan et al., Treatment of active Crohn's disease with MLN0002, a humanized antibody to the alpha4beta7 integrin, *Clin Gastroenterol Hepatol.*, 6(12):1370-7 (2008).
Fedyk et al., Exclusive antagonism of the alpha4beta7 integrin by vedolizumab confirms the gut-selectivity of this pathway in primates. *Inflamm Bowel Dis.*, N18(11):2107-19 (2012).
Fuh et al., 703 Gut-Homing CD4+ Lymphocytes Are Specifically Targeted in Cynomolgus Monkeys Dosed with Anti-Beta7 Antibodies, *Gastroenterology*, 134(4)1:A-99 (2008).
Harlow et al., Antibodies: A Laboratory Manual, Cold Spring Harbor Laboratory Press, Cold Spring Harbor, New York, (1990).
Honegger et al., Yet Another Numbering Scheme for Immunoglobulin Variable Domains: An Automatic Modeling and Analysis Tool, *J. Mol. Biol.*, 309(3):657-670 (2001).

(Continued)

*Primary Examiner* — Christine J Saoud
*Assistant Examiner* — Jon M Lockard
(74) *Attorney, Agent, or Firm* — Marshall, Gerstein & Borun LLP

(57) ABSTRACT

There is provided a method of treating a subject afflicted with a condition that is associated with inappropriate trafficking of cells expressing alpha4beta7 to the gastrointestinal tract, comprising administering to the subject an alpha4beta7 heterodimer specific antibody in an amount and at an interval sufficient to ameliorate the condition.

23 Claims, 9 Drawing Sheets

(56) References Cited

OTHER PUBLICATIONS

Kabat et al. Sequences of Proteins of Immunological Interest, 5th Ed., US Dept. of Health and Human Services, PHS, NIH, NIH Publication No. 91-3242, (1991).
Kenakin et al., UNIT 1.2 Receptor Theory, Current Protocols in Pharmacology, John Wiley & Sons, Inc., Hoboken, NJ, USA (2001).
Lefranc et al., IMGT unique numbering for immunoglobulin and T cell receptor constant domains and Ig superfamily C-like domains. *Dev Comp Immunol.*, 29:185-203 (2005).
Maharshak et al., Comparative analysis of Bayer wide-range C-reactive protein (wr-CRP) and the Dade-Behring high sensitivity C-reactive protein (hs-CRP) in patients with inflammatory bowel disease. *J Dig Dis.*, 9:140-3 (2008).
Paul, Fundamental immunology. 2nd ed. *Raven Press*, N.Y. (1989).
Pan et al., Su2082 Pharmacokinetics (PK), Pharmacodynamics (PD), and Safety of Amg 181, a Fully Human Anti-alpha4beta7 Antibody for Treating Inflammatory Bowel Diseases (IBD), *Gastroenterology*, 142(5)1:S565 (2012).
Pan et al., Pharmacology of AMG 181, a human anti-alpha4 beta7 antibody that specifically alters trafficking of gut-homing T cells, *Br J Pharmacol.*, 169(1):51-68 (2013).
Remington et al., Remington's Pharmaceutical Sciences, 16th Ed. Mack Publishing Company, Easton, Pennsylvania, (1980).
Sambrook et al., Molecular Cloning: A Laboratory Manual, 2d ed., Cold Spring Harbor Laboratory Press, Cold Spring Harbor, New York, (1989).
Sandborn et al., Natalizumab induction and maintenance therapy for Crohn's disease. *N Engl J Med.*, 353 (18):1912-25 (2005).
Schroeder et al., Coated oral 5-aminosalicylic acid therapy for mildly to moderately active ulcerative colitis. A randomized study. *N Eng J Med.*, 317 (26):1625-9 (1987).
Soler et al., The binding specificity and selective antagonism of vedolizumab, an anti-alpha4beta7 integrin therapeutic antibody in development for inflammatory bowel diseases. *J Pharmacol Exp Ther.*, 330(3):864-75 (2009).
Stefanich et al., A humanized monoclonal antibody targeting the beta7 integrin selectively blocks intestinal homing of T lymphocytes. *Br J Pharmacol.* 162(8):1855-70 (2011).
Targan et al., Natalizumab for the treatment of active Crohn's disease: results of the Encore Trial. *Gastroenterology*, 132(5):1672-83 (2007).
Thornton et al., Prediction of progress at last, *Nature*, 354(6349):105-6 (1991).
Vieira et al., Inflammatory bowel disease activity assessed by fecal calprotectin and lactoferrin: correlation with laboratory parameters, clinical, endoscopic and histological indexes. *BMC Res Notes*, 2:221 (2009).
International Preliminary Report on Patentability, PCT/US2012/066345, dated May 27, 2014.
International Search Report and Written Opinion, PCT/US2012/066345, dated Jul. 31, 2013.

\* cited by examiner

SEQUENCE LISTING

```
<160> NUMBER OF SEQ ID NOS: 8

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Val Phe Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Gly Ala Ser Ser Leu Gln Asn Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 2
<211> LENGTH: 107
<212> TYPE: PRT
<213> ORGANISM: Homo sapiens
```

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asn Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 3
<211> LENGTH: 108
<212> TYPE: PRT
<213> ORGANISM: Homo sapiens

<400> SEQUENCE: 3

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Pro
                85                  90                  95

Leu Thr Phe Gly Gly Gly Thr Lys Val Glu Ile Lys
            100                 105

<210> SEQ ID NO 4
<211> LENGTH: 118
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Val Thr Asp Leu
            20                  25                  30

Ser Met His Trp Val Arg Gln Ala Pro Gly Lys Gly Leu Glu Trp Met
        35                  40                  45

Gly Gly Phe Asp Pro Gln Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Arg Ser Leu Arg Ser Glu Asp Thr Ala Val Tyr Tyr Cys
                85                  90                  95

Thr Thr Glu Ser Ser Ser Ala Trp Phe Asp Pro Trp Gly Gln Gly Thr

```
                100                 105                 110

Leu Val Thr Val Ser Ser
        115

<210> SEQ ID NO 5
<211> LENGTH: 118
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Asp Leu
            20                  25                  30

Ser Ile His Trp Val Arg Gln Ala Pro Gly Lys Gly Leu Glu Trp Met
        35                  40                  45

Gly Gly Phe Asp Pro Gln Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Lys Ser Glu Asp Thr Ala Val Tyr Tyr Cys
                85                  90                  95

Ala Thr Gly Ser Ser Ser Ser Trp Phe Asp Pro Trp Gly Gln Gly Thr
            100                 105                 110

Leu Val Thr Val Ser Ser
        115

<210> SEQ ID NO 6
<211> LENGTH: 120
<212> TYPE: PRT
<213> ORGANISM: Homo sapiens

<400> SEQUENCE: 6

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Leu
        35                  40                  45

Ser Tyr Ile Ser Asn Ser Gly Ser Ala Met Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Ser Ser Gly Trp Phe Phe Glu Ser Trp Gly Gln
            100                 105                 110

Gly Thr Leu Val Thr Val Ser Ser
        115                 120

<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 8
<211> LENGTH: 326
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

-continued

```
            275                 280                 285
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

ADMINISTRATION OF ALPHA4BETA7 HETERO-DIMER-SPECIFIC ANTIBODY

FIELD OF THE INVENTION

The present invention relates in general to alpha4beta7 and MAdCAM and to inhibitors of the interaction thereof.

BACKGROUND OF THE INVENTION

Inflammatory bowel disease (IBD) comprises two types of chronic intestinal disorders: Crohn's disease (CD) and ulcerative colitis (UC). The hallmark of active IBD is a pronounced infiltration of innate immune cells (neutrophils, macrophages, dendritic cells, and natural killer T cells) and adaptive immune cells (B cells and T cells) into the lamina propria. Naïve and effector/memory T cells have distinct repertoires of trafficking ligands and receptors that restrict their ability to interact with specialized microvessels in different anatomical compartments. Consequently, they have distinct patterns of migration.

T cells that become activated in mesenteric lymph nodes and Peyer's patches become "gut-tropic" cells after they start expressing the integrin alpha4beta7. While alpha4beta7 is expressed, at various levels, on peripheral T cells, B cells, natural killer cells, and eosinophils, as well as on naïve T cells in peripheral blood, alpha4beta7 is most highly expressed on a subpopulation of CD4+CD45RA− memory T cells, which is believed to play a critical role in the pathogenesis of IBD (Abraham and Cho, *N Engl J Med.* 2009; 61:2066).

The ligand for alpha4beta7 is the addressin mucosal addressin cell adhesion molecule (MAdCAM-1), a member of the immunoglobulin superfamily. This addressin is primarily expressed on the postcapillary venules of the intestinal lamina propria, the mesenteric lymph nodes, and in Peyer's patches; expression is upregulated in the chronically inflamed small and large intestine of subjects with UC and Crohn's disease (Briskin et al, *Am J Pathol.* 1997; 151:97; Arihiro et al, *Pathol Int.* 2002; 52:367).

The importance of alpha4beta7-MadCAM-1 interactions for memory lymphocyte homing to the gut have been shown in preclinical models as well as in man. Tysabri®, a monoclonal antibody targeting the alpha4 component of the alpha4beta1 and alpha4beta7 heterodimeric receptors, significantly improved symptoms in a population of active Crohn's disease subjects (Sandborn et al, *N Engl J Med* 2005; 353:1912; Targan et al, *Gastroenterology* 2007; 132: 1672). MLN0002, a humanized monoclonal antibody specifically targeting alpha4beta7, was shown to induce disease remission in both UC and Crohn's disease subjects (Feagan et al, *Clin Gastroenterol Hepatol.* 2008; 6:1370; Feagan et al, *N Engl J Med.* 2005; 352:2499).

Both of these agents, however, present certain drawbacks. Development of progressive multifocal leukoencephalopathy (PML) in subjects treated with Tysabri® is likely due to inhibition of leukocyte trafficking to the brain. Moreover, MLN0002 induced strong immune responses that contributed to early clearance of the antibody resulting in loss of efficacy. This, together with the potential for severe functional consequences of surgery and drawbacks for other agents used in treating IBD, calls for the development of new therapeutic modalities in IBD.

SUMMARY OF THE INVENTION

Figure 1:
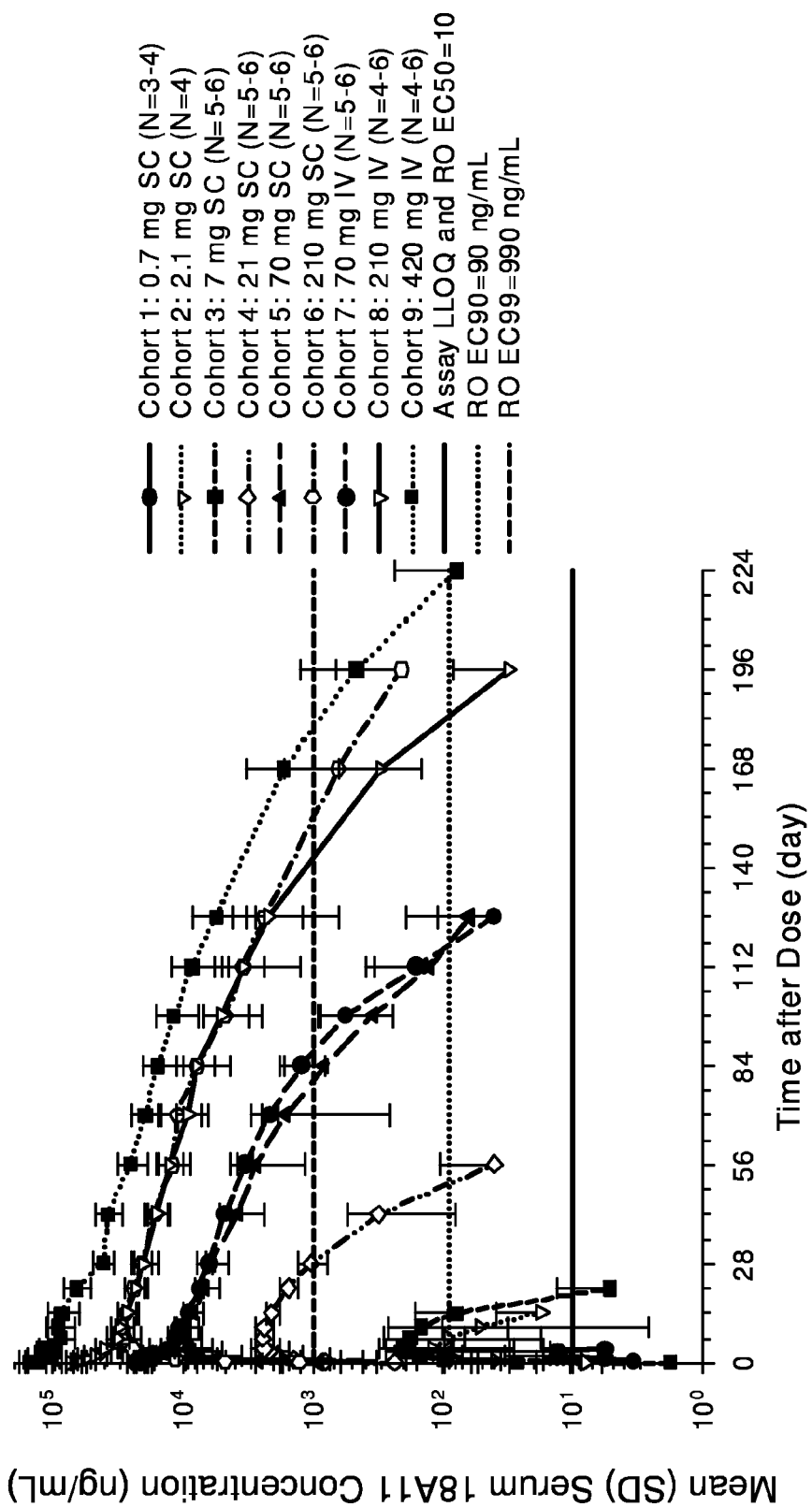
FIG. 1 presents the results of the pharmacokinetic analysis of an ascending single dose study of 18A11 in healthy subjects (HS). The results shown illustrate the mean (+/−SD) serum 18A11 Concentration-Time Profiles.

There is provided a method of treating a subject afflicted with a condition that is associated with inappropriate trafficking of cells expressing alpha4beta7 to the gastrointestinal tract comprising administering to the subject an amount of an alpha4beta7 heterodimer specific antibody in an amount and at an interval selected from the group consisting of: 5-14 mg every 7-21 days; 15-54 mg every 14-56 days; 55-149 mg every 43-126 days; 150-299 mg every 112-147 days; and 300-1000 mg every 126-224 days s. In another aspect of the invention, the amount and interval are selected from the group consisting of: 5-10 mg every 11-17 days; 15-30 mg every 30-50 days 55-85 mg every 75-95 days; 160-260 mg every 120-132 days; and 300-700 mg every 165-185 days. In a further embodiment of the invention, the amount and interval are selected from the group consisting of: 7 mg every two weeks; 21 mg every six weeks; 70 mg every 12 weeks; 210 mg every 18 weeks; and 420 mg every six months. In one embodiment, the alpha4beta7 heterodimer specific antibody is 18A11.

The invention also provides a method of treating a subject afflicted with a condition that is associated with inappropriate trafficking of cells expressing alpha4beta7 to the gastrointestinal tract comprising administering to the subject an amount of an alpha4beta7 heterodimer specific antibody in an amount and at an interval sufficient to achieve and/or maintain a receptor occupancy of at least about 75%; at least about 80%; at least about 85%; at least about 90%; at least about 95%.; or at least about 99%. In one embodiment, the alpha4beta7 heterodimer specific antibody is 18A11.

Further provided is a method of treating a subject afflicted with a condition that is associated with inappropriate trafficking of cells expressing alpha4beta7 to the gastrointestinal tract comprising administering to the subject an amount of an alpha4beta7 heterodimer specific antibody in an amount and at an interval sufficient to achieve and/or maintain a quantity of heterodimer-specific antibody per volume of serum of between 10 ng/ml and 1000 ng/ml. In one aspect of the invention, the quantity of heterodimer-specific antibody per volume of serum is at least 10 ng/ml; at least 25 ng/ml; at least 50 ng/ml; at least 60 ng/ml; at least 70 ng/ml; at least 75 ng/ml; at least 80 ng/ml; at least 85 ng/ml; at least 90 ng/ml; at least 95 ng/ml; at least 100 ng/ml; at least 150 ng/ml; at least 200 ng/ml; at least 500 ng/ml or at least 990 ng/ml. In one embodiment, the alpha4beta7 heterodimer specific antibody is 18A11.

The invention also provides a method of treating a subject afflicted with a condition that is associated with inappropriate trafficking of cells expressing alpha4beta7 to the gastrointestinal tract comprising administering to the subject an amount of an alpha4beta7 heterodimer specific antibody in an amount and at an interval sufficient to achieve/maintain a quantity of heterodimer-specific antibody per volume of serum is selected from the group consisting of: at least 25 ng/ml; at least 50 ng/ml; at least 60 ng/ml; at least 70 ng/ml; at least 75 ng/ml; and at least 80 ng/ml. Althernatively, the quantity of heterodimer-specific antibody per volume of serum is between 85 ng/ml and 100 ng/ml; between 70 ng/ml and 150 ng/ml; between 50 ng/ml and 250 ng/ml; between 40 ng/ml and 500 ng/ml; between 25 ng/ml and 750 ng/ml; or between 10 ng/ml and 1000 ng/ml.

Further provided is a method of treating a subject afflicted with a condition that is associated with inappropriate trafficking of cells expressing alpha4beta7 to the gastrointestinal tract comprising administering to the subject an amount of an alpha4beta7 heterodimer specific antibody, wherein the alpha4beta7 heterodimer specific antibody is 18A11. In a further embodiment, 18A11 is an isolated, alpha4beta7 heterodimer-specific antigen binding protein having a heavy chain variable region comprising CDR1, CDR2 and CDR3 from SEQ ID NO:5, and a light chain variable region comprising CDR1, CDR2 and CDR3 from SEQ ID NO:2. Alternatively, 18A11 is an isolated, alpha4beta7 heterodimer-specific antigen binding protein wherein the heavy chain variable region is at least 90% identical to SEQ ID NO:5, and the light chain variable region is at least 90% identical to CDR1, CDR2 and CDR3 to SEQ ID NO:2. The method further includes administering 18A11 wherein 18A11 further comprises a light chain constant region (SEQ ID NO:7) and a heavy chain constant region (SEQ IN NO:8); additionally (or alternatively) wherein 18A11 differs in amino acid sequence from the amino acid sequences of SEQ ID NO:2 and 5 by the substitution, insertion or deletion of from 1 to 10 amino acids in an 18A11 variable region; additionally (or alternatively) wherein 18A11 differs in amino acid sequence from the amino acid sequences of SEQ ID NO:7 and 8 by the substitution, insertion or deletion of from 1 to 10 amino acids in an 18A11 constant region of 18A11 and additionally (or alternatively) wherein the 18A11 incorporate one or more modifications selected from the group consisting of conversion of some, most or substantially all of an N-terminal amino acid to pyroglutamic acid; and removal (either post-translationally or by recombinant technology) of one, two, three, four or five N-terminal and/or C-terminal amino acids.

Also provided herein is a method to assess alpha4beta7 receptor occupancy in a human subject being treated with an alpha4beta7heterodimer-specific antibody, comprising: preparing a set of six reagent tubes for the subject, the tubes being numbered 1 though 6, each tube containing alpha4beta7heterodimer-specific antibody (tube 2; referred to as 'spiked') or placebo control (tubes 1, 3, 4, 5 and 6) and obtaining a sample of whole blood from a subject that has been treated with an alph4beta7 heterodimer-specific antibody and placing a portion of the sample of whole blood into each of the six tubes to form a sample mixture and incubating the resultant sample mixture; adding antibody cocktail plus phycoerythrin reagent at a ratio of 1:1 to the sample mixture, in a scheme substantially as shown, to form an antibody cocktail/sample mixture (to tube 1 is added anti CD8+CD103; FITC, a competing anti-alpha4beta7 antibody:phycoerythrin, Anti-CD45:PerCP, anti-CCR7:AlexaFluor® 647, anti CD45 RA:APC-H7, and antiCD3:V450; to tube 2 is added anti CD8+CD103:FITC, a competing anti-alpha4beta7 antibody:phycoerythrin, Anti-CD45:PerCP, anti-CCR7:AlexaFluor® 647, anti CD45 RA:APC-H7, and antiCD3:V450; to tube 3 is added anti CD+CD103: FITC, a non-competing anti-beta7 antibody:phycoerythrin, Anti-CD45:PerCP, anti-CCR7:AlexaFluor® 647, anti CD45 RA:APC-H7, and antiCD3:V450; to tube 4 is added anti CD7+CD103:FITC, a non-competing anti-beta7 antibody: phycoerythrin, Anti-CD45:PerCP, anti CD45 RA:APC-H7, and antiCD3:V450; to tube 5 is added anti CLA:FITC, a non-competing anti-beta7 antibody:phycoerythrin, Anti-CD45:PerCP, anti-CD4:AlexaFluor® 647, anti CD45 RA:APC-H7, and antiCD3:V450; to tube 6 is added anti CD19:FITC, anti-CD4:phycoerythrin, Anti-CD45:PerCP, anti-CD16+CD56:AlexaFluor® 647, anti CD8 RA:APC-H7, and antiCD3:V450); incubating the antibody cocktail/ sample mixture; treating the antibody cocktail/sample mixture to lyse any red blood cells that are present to form a mixture of remaining cells; washing the mixture of remaining cells and analyzing them using a fluorescent activated cell sorter to determine the percentage of alpha4beta7 receptor present on the remaining cells that is occupied by the alpha4beta7heterodimer-specific antibody.

In one such method to assess alpha4beta7 receptor occupancy the sample mixture is incubated at room temperature for approximately 30 minutes, and the antibody cocktail/ sample is incubated at room temperature for approximately 20 minutes. Alternatively or additionally, the portion of the whole blood sample added to each tube is 100 microliters, the volume of antibody cocktail is 20 microliters, and the volume of antibody:phycorerythrin reagent is 60 microliters. Alternatively or additionally, the number of CD4 naïve T cell events collected for each population is divided by the lymphocyte events and then multiplied by hematology result of lymphocytes per microliter, wherein naïve CD4 T cells are defined as CCR7+ CD45RA+ CD3+ CD8− CD103− CD45+ lymphocytes, and Alternatively or additionally, the median fluorescence intensity values for spiked and non-spiked conditions are converted to molecules bound per cell (MBPC) using a fluorescent bead standard curve and then utilized to calculate receptor occupancy. Alternatively or additionally, there are two pre-dose samples available for the subject, and target saturation is calculated using the following equation:

$$\frac{(MBPC \text{ non-spiked} - MBPC \text{ spiked}) \text{ Post-dose}}{\{(MBPC \text{ non-spiked} - MBPC \text{ spiked}) \text{Pre-}d1 + (MBPC \text{ non-spiked} - MBPC \text{ spiked}) \text{Pre-}d2\}/2}$$

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. An abbreviated table of terms commonly used in the art of clinical studies is shown in Table 1 below.

TABLE 1

Commonly Used Terms

| | |
|---|---|
| AE(s) | Adverse Event(s) |
| ADA | Anti-drug antibody |
| AUC | Area under the drug concentration-time curve |
| $AUC_{tau}$ | Area under the drug concentration-time curve within each dosing interval at steady state |
| $C_{max}$ | Maximum observed concentration in serum |
| CM | Central Memory |
| Day −1 | Day before dosing |
| Day 1 | First day investigational product is administered to the subjects |
| $EC_{50}$ | Concentration producing 50% of the maximum effect |
| $EC_{90}$ | Concentration producing 90% of the maximum effect |
| $EC_{99}$ | Concentration producing 99% of the maximum effect |
| EOS | End of Study |
| FIH | First in Human |
| GLP | Good Laboratory Practice |
| HAHA | Human Anti-Human Antibodies |
| HIV | Human Immunodeficiency Virus |
| IV | Intravenous |
| KLH | Keyhole Limpet Hemocyanin |
| LFCV | Last Full Clinical Visit |
| MAdCAM-1 | Mucosal Addressin Cell Adhesion Molecule-1 |
| NOAEL | No Observed Adverse Event Level |
| PD | Pharmacodynamics |
| PK | Pharmacokinetics |
| PML | Progressive multifocal leucoencephalopathy |
| Q28D | Once every 28 days |
| RO | Receptor occupancy |
| SC | Subcutaneous |
| $T_{max}$ | Time of maximum concentration |

The term "efficacy" as used herein in the context of a dosage regime refers to the effectiveness of a particular treatment regime. Efficacy can be measured based on change the course of the disease in response to an agent of the present invention. In one embodiment, an antigen binding protein (for example, an alpha4beta7 heterodimer specific antibody) is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question.

In one embodiment, an improvement is considered to be sustained if the subject exhibits the improvement on at least two occasions separated by two to four weeks. In another embodiment, an improvement is considered to be sustained if the subject exhibits the improvement on at least two occasions separated by two to four months; in a further embodiment, an improvement is considered to be sustained if the subject exhibits the improvement on at least two occasions separated by six to twelve months. The degree of improvement generally is determined by a physician, who may make this determination based on signs, symptoms, biopsies, or other test results, and who may also employ questionnaires that are administered to the subject, such as quality-of-life questionnaires developed for a given disease.

The terms "treating", and "treatment" and the like are used herein to generally mean obtaining a desired pharmacological or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease and/or its symptoms or conditions. The invention is directed towards treating a patient's suffering from disease related to pathological inflammation. The present invention is involved in preventing, inhibiting, or relieving adverse effects attributed to pathological inflammation over long periods of time and/or are such caused by the physiological responses to inappropriate inflammation present in a biological system over long periods of time.

Where a range of values is provided, it is understood that each intervening value (to the tenth of the unit of the lower limit unless the context clearly dictates otherwise) between the upper and lower limit of that range, and any other stated or intervening value or smaller range, in that stated range is encompassed within the invention. The upper and lower limits of smaller ranges may independently be included in the smaller range, subject to any specifically excluded limit in the stated range. Where the stated range includes one or both of the limits, ranges excluding either both of those included limits are also included in the invention.

The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The terms "alpha4beta7 inhibitor" and "alpha4beta7 antagonist" are used interchangeably. Each is a molecule that detectably inhibits at least one function of alpha4beta7. The inhibition caused by an alpha4beta7 inhibitor need not be complete so long as it is detectable, for example by using an assay. Any assay of a function of alpha4beta7 can be used; several are well-known in the art. Examples of functions of alpha4beta7 that can be inhibited by an alpha4beta7 inhibitor include ligand binding (i.e., binding to MAdCAM-1), adhesion to ligand-expressing cells, trafficking to a particular compartment such as the gut, release of cytokines, chemokines and other mediators, enhancing or exacerbating inflammatory response and tissue damage, and so on. Examples of types of alpha4beta7 inhibitors and alpha4beta7 agonists include, but are not limited to, alpha4beta7 binding polypeptides such as antigen binding proteins (e.g., alpha4beta7 antigen binding proteins), antibodies, antibody fragments, and antibody derivatives. Additional examples include alpha4beta7 heterodimer-specific antibodies and variants thereof.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins and biologically active fragments (for example, fragments of an antibody that retain the ability to bind antigen). A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and/or glycosylation. Unless otherwise indicated, the term "antibody" includes, in addition to antibodies comprising two full-length heavy chains and two full-length light chains, derivatives, variants, fragments, and muteins thereof, examples of which are described below.

Polypeptides useful in the invention include polypeptides (including variants) that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). Consensus sequences can be used to select amino acid residues for substitution; those of skill in the art recognize that additional amino acid residues may also be substituted.

Modifications also include conservative amino acid substitutions. A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

In one embodiment, a useful polypeptide has an amino acid sequence that is 85%, 90%, 92%, 95%, 98%, 99% or 100% identical to a polypeptide disclosed herein. In another embodiment, a useful polypeptide is between 85% and 100% identical to a polypeptide disclosed herein. The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters. In another embodiment, a useful polypeptide differs from a polypeptide disclosed herein by substitution, deletion or insertion of from one to five amino acids. Such substitution, deletion or insertion may occur at either termini of the disclosed polypeptide (for example, the addition of an N-terminal methionine, deletion of a C-terminal lysine, addition or deletion of an internal amino acid, and/or substitution of an amino acid with a different amino acid). When the useful polypeptide comprises more than one polypeptide (for example, an antibody comprising two heavy chains and two light chains), each polypeptide may be modified by deletion, insertion or substitution of from one to five amino acids. In a further embodiment, up to ten amino acids may be substitute, deleted or inserted. Useful polypeptides will exhibit at least one activity of the alpha4beta7 antagonists described here, for example, inhibition of one or more of ligand binding, adhesion to ligand-expressing cells, trafficking to a particular compartment such as the gut, or release of cytokines, chemokines and other mediators, and additionally or alternatively ameliorating an inflammatory response or tissue damage, and so on.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alio, Fab, Fab', F(ab')$_2$, Fv, domain antibodies (dAbs), and complementarity determining region (CDR) fragments, variable region fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

An "immunoglobulin" is a multimeric molecule. In a naturally occurring immunoglobulin, each multimer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5th Ed., US Dept. of Health and Human Services, PHS, NIH, NIH Publication no. 91-3242, 1991. Other numbering systems for the amino acids in immunoglobulin chains include IMGT® (the international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

An antibody "specifically binds" to an antigen (e.g., human alpha4beta7) if it binds to the antigen with a dissociation constant of 1 nanomolar or less. As used herein, an antibody is "heterodimer specific" if it binds to a first heterodimeric integrin but not to other integrins that share one chain with the first integrin. For example, an antibody that is alpha4beta7 heterodimer specific will bind to alpha4beta7 but not to alpha4beta1 or alphaEbeta7. In one embodiment, the antibody is a monoclonal antibody; in another embodiments the antibody is a selected monoclonal antibody (MAB) comprising an amino acid sequence as shown in Tables 2a (light chain variable region) and 2b (heavy chain variable region), or a variant as herein described. In another embodiment the MAB further comprises a light chain constant region (SEQ ID NO:7) and a heavy chain constant region (SEQ IN NO:8). The assignment of amino acids to each domain in the tables below is in accordance with the definitions of Kabat et al. in *Sequences of Proteins of Immunological Interest*, 5th Ed., US Dept. of Health and Human Services, PHS, NIH, NIH Publication no. 91-3242, 1991. Other numbering systems for the amino acids in immunoglobulin chains include IMGT® (the international ImMunoGeneTics information system; Lefranc et al, *Dev. Comp. Immunol.* 29:185-203; 2005) and AHo (Honegger and Pluckthun, *J. Mol. Biol.* 309(3):657-670; 2001). Those of skill in the art recognize that the borders between CDRs and FRs can vary from one to five amino acids from that shown.

TABLE 2a

Selected MAB light chains

| Light chain | FR1 | CDR1 | FR2 |
|---|---|---|---|
| 2F12 K | DIQMTQSPSSVFASVGDRVTITC | RASQGISSWLA | WYQQKPGKAPNLLIY |
| 18A11 K | DIQMTQSPSSVSASVGDRVTITC | RASQGISSWLA | WYQQKPGKAPKLLIY |
| 17C8 K | EIVMTQSPATLSVSPGERATLSC | RASQSVSSNLV | WYQQKPGQAPRLLIY |

| Light chain | CDR2 | FR3 | CDR3 | FR4 |
|---|---|---|---|---|
| 2F12 K | GASSLQN | GVPLRFSGSGSGTDFTLTISSLQPEDFATYYC | QQANSFPWT | FGQGTKVEIK |
| 18A11 K | GASNLES | GVPSRFSGSGSGTDFTLTISSLQPEDFANYYC | QQANSFPWT | FGQGTKVEIK |
| 17C8 K | GASTRAT | GIPARFSGSGSGTDFTLTISSLQSEDFAVYYC | QQYDDWPPLT | FGGGTTVEIK |

TABLE 2b

Selected MAB heavy chains

| Heavy chain | FR1 | CDR1 | FR2 |
|---|---|---|---|
| 2F12 H | QVQLVQSGAEVKKPGASVKVSCKVSGYTVT | DLSMH | WVRQAPGKGLEWMG |
| 18A11 H | QVQLVQSGAEVKKPGASVKVSCKVSGYTLS | DLSIH | WVRQAPGKGLEWMG |
| 17C8 H | QVQLVESGGGLVKPGGSLRLSCAASGFTFS | DYYMS | WIRQAPGKGLEWLS |

| Heavy chain | CDR2 | FR3 |
|---|---|---|
| 2F12 H | GFDPQDGETIYAQKFQG | RVTMTEDTSTDTAYMELRSLRSEDTAVYYCTT |
| 18A11 H | GFDPQDGETIYAQKFQG | RVTMTEDTSTDTAYMELSSLKSEDTAVYYCAT |
| 17C8 H | YISNSGSAMYYADSVKG | RFTISRDNARNSLYLQMNSLRAEDTAVYYCAR |

TABLE 2b-continued

Selected MAB heavy chains

| Heavy | CDR3 | FR4 |
|---|---|---|
| 2F12 H | ESSSAWFDP | WGQGTLVTVSS |
| 18A11 H | GSSSSWFDP | WGQGTLVTVSS |
| 17C8 H | EYSSGWFFFES | WGQGTLVTVSS |

These, and other alpha4beta7 heterodimer specific antigen binding proteins are disclosed in U.S. patent application Ser. No. 12/725,031 (published as US20100254975), the disclosure of which is incorporated by reference herein. The antibodies disclosed in Table 2 are human antibodies that specifically recognize the alpha4beta7 heterodimer, but do not bind either α4β1 or αEβ7. 18A11 binds alpha4beta7 with high affinity and blocks the alpha4beta7 interaction with MAdCAM-1. 18A11 potently inhibits MAdCAM-1-mediated T cell adhesion, but does not inhibit VCAM-1-mediated T cell adhesion. The 18A11 formulation also enables SC administration.

As used herein, in accordance with previous definitions of peptides, immunoglobulins, antibodies and the like, "alpha4beta7 heterodimer specific antigen binding proteins" refers to an intact immunoglobulin or to an antigen binding portion thereof that competes with the intact antibody for specific binding, unless otherwise specified. "18A11" also comprehends antibodies (or fragments thereof) that are identical or similar to 18A11 in amino acid sequence, particularly in the variable regions, or in the CDRs thereof (however, variations in the constant regions are also contemplated). For example, a useful 18A11 polypeptide has an amino acid sequence that is 85%, 90%, 92%, 95%, 98%, 99% or 100% identical to that of an 18A11 polypeptide disclosed herein (for example, as in Tables 2a and 2b). In another embodiment, a useful polypeptide is between 85% and 100% identical to 18A11. In one embodiment, 18A11 is an isolated, alpha4beta7 heterodimer-specific antigen binding protein having a heavy chain variable region comprising CDR1, CDR2 and CDR3 from SEQ ID NO:5, and a light chain variable region comprising CDR1, CDR2 and CDR3 from SEQ ID NO:2. In another embodiment, 18A11 is an isolated, alpha4beta7 heterodimer-specific antigen binding protein wherein the heavy chain variable region is at least 90% identical to SEQ ID NO:5, and the light chain variable region is at least 90% identical to CDR1, CDR2 and CDR3 to SEQ ID NO:2.

In a further aspect, 18A11 may differ in amino acid sequence from the amino acid sequence disclosed herein by the substitution, insertion or deletion of from 1 to 10 amino acids in an 18A11 variable region. In one aspect of the invention, from one to 10 amino acids may be deleted, substitute or inserted in the constant region of 18A11. Moreover, the afore mentioned substitutions, insertions or deletions may be combined (i.e., can be made in either or both the variable and constant regions). Further embodiments include polypeptides that incorporate one or more post-translational modifications, including conversion of some, most or substantially all of an N-terminal amino acid to pyroglutamic acid, removal (either post-translationally or by recombinant technology) of one, two, three, four or five N-terminal and/or C-terminal amino acids.

In another aspect, the present invention provides a pharmaceutical composition comprising the antibody and one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. Additionally, the formulation of the pharmaceutical composition may depend on the route of administration; suitable components are nontoxic to recipients at the dosages and concentrations employed. Accordingly, the composition may be formulated as a lyophilizate using appropriate excipient solutions (e.g., sucrose) as diluents, or as a suppository that can include vehicles such as cocoa butter, carbowaxes and polyethylene glycols, which melt at body temperature, yet are solidified at room temperature. Additionally, the alpha4beta7 heterodimer specific antibody may be formulated in solid, semi-solid, liquid or gaseous forms (including tablets, capsules, powders, granules, ointments, solutions, suspensions, injections, inhalants, gels, microspheres, and aerosols). Further examples of components that may be employed in pharmaceutical formulations are presented in Remington's Pharmaceutical Sciences, 16$^{th}$ Ed. (1980) and 20$^{th}$ Ed. (2000), Mack Publishing Company, Easton, Pa.

The pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or cutaneous routes (including intra-, trans- or sub-dermal, and subcutaneous), by bolus injection, or continuous infusion. In further embodiments, the compositions are administered by oral, buccal, rectal, intratracheal, gastric, or intracranial routes. Localized administration, e.g. at a site of disease or injury is contemplated, for example, by enema or suppository for conditions involving the gastrointestinal tract. Also contemplated are transdermal delivery and sustained release from implants. Delivery by inhalation includes, for example, nasal or oral inhalation, use of a nebulizer, inhalation of the antagonist in aerosol form, and the like. Other alternatives include eye-drops; oral preparations including pills, syrups, lozenges or chewing gum; and topical preparations such as lotions, gels, sprays, and ointments.

In one aspect, the present invention provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). In one embodiment, the present invention provides a method of treating a condition in a subject comprising administering the pharmaceutical composition comprising an alpha4beta7 heterodimer specific antibody to the subject, wherein the condition is treatable by reducing the activity (partially or fully) of alpha4beta7 in the subject. Treating encompasses both therapeutic administration (i.e., administration when signs and symptoms of the disease or condition are apparent) as well prophylactic or maintenance therapy (i.e., administration when the disease or condition is quiescent), as well as treating to induce remission and/or maintain remission. Accordingly, the severity of the disease or condition can be reduced (partially, significantly or completely), or the signs and symptoms can be prevented or delayed (delayed onset, prolonged remission, or quiescence).

Among the conditions to be treated in accordance with the present invention are conditions characterized by inappropriate expression or activity of alpha4beta7. Such conditions include those that are associated with inappropriate trafficking of cells, for example, the trafficking of leukocytes (such as lymphocytes or monocytes) to the gastrointestinal tract or other tissues comprising cells that express MAdCAM-1 (as a result of binding of the leukocytes to the cells that express MAdCAM-1). Diseases which can be treated accordingly include inflammatory bowel disease (IBD), such as ulcerative colitis (UC), Crohn's disease (CD), Celiac disease (nontropical Sprue), enteropathy associated with seronegative arthropathies, microscopic or collagenous colitis, eosinophilic gastroenteritis, or pouchitis resulting after proctocolectomy and ileoanal anastomosis. Additional conditions that may be treated in accordance with the present invention include pancreatitis, insulin-dependent diabetes mellitus, mastitis, cholecystitis, cholangitis, pericholangitis, chronic bronchitis, chronic sinusitis, asthma and graft versus host disease.

Disease activity in CD is estimated using the Crohn's Disease Activity Index (CDAI). The CDAI is a weighted, composite index of eight items (stool frequency, severity of abdominal pain, degree of general well-being, presence or absence of extraintestinal manifestations or fistula, use or nonuse of antidiarrheal agents, presence or absence of an abdominal mass, hematocrit, and body weight), with scores ranging from approximately 0 to 600, with a higher score indicating more severe disease activity. Typically, patients with scores <150 are considered in remission. Disease is otherwise graded as mild, moderate, or severe with scores of 151-to-219, 220-to-449, and equal or greater than 450, respectively. Induction therapy for patients with mild-to-moderate CD typically uses 5-aminosalicylates or sulfasalazine or antimicrobial agents. Disease activity in UC is estimated using scores such as the Mayo score (originally described by Schroeder et al., N Eng J Med. 317:1625; 1987), a composite index of four items (stool frequency, rectal bleeding, endoscopy findings, and physician global assessment) with each item graded semi-quantitatively on a score of 0 to 3 for a maximal total score of 12. The goals of therapy in UC are the same as those cited for CD namely induction and maintenance therapy. The therapies available are similar to those for CD.

The alpha4beta7 heterodimer specific antibody may be administered to achieve an improvement in a subject's condition. Improvement may be indicated by a decrease in an index of disease activity, such as CDAI or Mayo score, by amelioration of clinical symptoms or by any other measure of disease activity. In one embodiment, an improvement is considered to be sustained if the subject exhibits the improvement on at least two occasions separated by two to four weeks. In another embodiment, an improvement is considered to be sustained if the subject exhibits the improvement on at least two occasions separated by two to four months; in a further embodiment, an improvement is considered to be sustained if the subject exhibits the improvement on at least two occasions separated by six to twelve months. The degree of improvement generally is determined by a physician, who may make this determination based on signs, symptoms, biopsies, or other test results, and who may also employ questionnaires that are administered to the subject, such as quality-of-life questionnaires developed for a given disease.

In another embodiment, treatment of a subject with an alpha4beta7 heterodimer specific antibody may be given in an amount and/or at sufficient interval to achieve and/or maintain a certain level of receptor occupancy (RO), for example using an assay as described herein. For example, the heterodimer specific antibody is given to achieve a receptor occupancy of at least 75%, at least 80%, at least 85%, at least 90%, at least 95% or at least 99%.

In a further embodiment, treatment of a subject with an alpha4beta7 heterodimer specific antibody may be given in an amount and/or at sufficient interval to achieve and/or maintain a certain quantity of heterodimer-specific antibody per volume of serum, using, for example, an assay as described herein. For example, the heterodimer specific antibody is given to achieve at least 10 ng/ml, 25 ng/ml, 50 ng/ml, 60 ng/ml, 70 ng/ml, 75 ng/ml, 80 ng/ml, 85 ng/ml, 90 ng/ml, 95 ng/ml, 100 ng/ml, 150 ng/ml, 200 ng/ml, 500 ng/ml, or 990 ng/ml. In a further embodiment, the heterodimer specific antibody is given to achieve from 10 ng/ml to 1000 ng/ml. Those of skill in the art will understand that the amounts given here apply to a full-length antibody or immunoglobulin molecule; if an antigen binding fragment thereof is used, the absolute quantity will differ from that given in a manner that can be calculated based on the molecular weight of the fragment.

In one embodiment, 18A11 is administered in an amount of 7 mg every two weeks. In a further example, 18A11 is administered every 7-21 days, every 11-17 days, every 13-15 days, or every 14 days. In one example of such an embodiment, the amount of 18A11 is in the range of 5-10 mg, or in the range of 5 to 14 mg. Further provided by the invention is the administration of 21 mg of 18A11 every six weeks, or every 14-56 days, or every 30-50 days; or every 40-44 days. Also provided as an example of such embodiment is administration of an amount in the range of 15-30 mg, or 15-54 mg.

In a further embodiment, 18A11 is administered in an amount of 70 mg every three months or twelve weeks. For example, 18A11 is administered every 43-126 days, or every 75-95 days, or every 80-88 days. In another aspect of such an embodiment, the amount of 18A11 is in the range of 55-85 mg, or in the range of 55-99 mg. Further provided by the invention is the administration of 210 mg of 18A11 every 18 weeks (or 4.5 months), or every 112-147 days, or every 120-132 days; or every 125-129 days. Also provided as an example of such embodiment is administration of amounts in the range of 160-260 mg, or 160-300 mg.

In a still further embodiment, 18A11 is administered in an amount 420 mg every 6 months. In yet another embodiment, 18A11 is administered every 126-224 days, or every 165-185 days, or every 160-174 days. In one example of such an embodiment, the amount of 18A11 is in the range of 300-700 mg, or in the range of 300-1000 mg. The administration of other amounts of 18A11, and at additional intervals of administration, are also contemplated.

Treatment of IBD includes lifestyle alterations, medical management, and surgical interventions. Accordingly, in another aspect, the present invention provides a method of treating a subject with an alpha4beta7 heterodimer specific antibody and one or more other treatments. In one embodiment, such a combination therapy achieves synergy or an additive effect by, for example, attacking multiple sites or molecular targets, or inhibiting multiple pathways. Types of combination therapies that can be used in connection with the present invention include inhibiting or activating (as appropriate) multiple nodes in a single disease-related pathway, multiple pathways in a target cell, and multiple cell types within a target tissue.

In one embodiment, a combination therapy method comprises administering to the subject two, or more alpha4beta7 antagonists (for example, two or more treatments that together inhibit, directly or indirectly alpha4beta7-mediated activity(ies)). Examples of such methods include using combinations of two or more alpha4beta7 heterodimer-specific antibodies, of an alpha4beta7 heterodimer-specific antibody and another antibody that binds alpha4beta7 or a subunit thereof (for example, an antibody that binds alpha4 or an antibody that binds beta7), or of an alpha4beta7 heterodimer-specific antibody and an antagonist, such as an antibody, of a binding partner of alpha4beta7 (for example, MAdCAM). Combinations of the alpha4beta7 heterodimer-specific antibody with other biologics is also contemplated. Examples of such biologics include antagonists, or agonists, as appropriate (for example, antagonistic antibodies, portions of receptors, and/or agonistic versions thereof) of cytokines, such as interleukins IL-1 through IL-35, tumor necrosis factors alpha and beta, interferons alpha, beta and gamma, tumor growth factor beta (TGF-beta), colony stimulating factor (CSF) and granulocyte monocyte colony stimulating factor (GM-CSF), as well as other antagonists of chemokines such as MCP-1, MIP-1alpha, MIP-1beta, RANTES, exotaxin and IL-8. Included herein as agents such as ustekinumab, briakinumab, infliximab, adalimumab, certolizumab pegol, natalizumab and vedolizumab. Such agent(s) may be administered parenterally or by another suitable route, at dosages and intervals that are known in the art and described in the prescribing information.

Additional types of combination may be employed with the alpha4beta7 antagonists described herein. Examples include using combinations of an alpha4beta7 heterodimer-specific antibodies and one or more other therapeutic moiety having anti-inflammatory properties (for example, non-steroidal anti-inflammatory agents, steroids, and/or immunomodulators), or of an alpha4beta7 inhibiting antigen binding protein and one or more other treatments (e.g., surgery, ultrasound, or treatment effective to reduce inflammation). Useful agents that may be combined with alpha4beta7 inhibitors include those used to treat, for example, Crohn's disease or ulcerative colitis, such as aminosalicylate (for example, mesalamine or substances that are metabolized to mesalamine, including, for example, Asacol®, salofalk, Pentasa®, Dipentum®, colazide, Lialda® and Rowasa®), corticosteroids/glucocorticoids (including prednisolone methasulfobenzoate, tixocortol pivalate, fluticasone propionate, beclomethasone dipropionate, and budesonide), antibiotics such as metronidazole or ciprofloxacin (or other antibiotics useful for treating, for example, patients afflicted with fistulas), and immunosuporessives such as azathioprine (for example, Imuran® and Azasan®), 6-mercaptopurine (for example, Purinethol®), methotrexate (for example, Trexall®, Rheumatrex®), tacrolimus (for example, Prograf®) and cyclosporine (for example, Gengraf®, Neoral®, and Sandimmune®). Combinations of such agents are also contemplated for use with the inventive alpha4beta7 inhibitors. Such agent(s) may be administered orally or by another route, for example via suppository or enema, at dosages and intervals that are known in the art and described in the prescribing information.

Furthermore, anti-alpha4beta7 antibodies or antibody derivatives, or the aforesaid combinations, can be used in conjunction with one or more molecules or other treatments, wherein the other molecule(s) and/or treatment(s) do not directly bind to or affect alpha4beta7, but which combination is effective for treating or preventing the condition being treated. For example, an alpha4eta7 inhibitor can be used in combination with probiotic therapy, or other therapy used to restore or maintain normal gut flora, including gut flora transplant. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. Such agent(s) or therapies may be administered by routes, and at dosages and intervals, that are known in the art and described in the prescribing information.

Additional supportive therapies are included in possible combination treatment with alpha4beta7 heterodimeric antibodies; such supportive therapies as (without limitation), analgesics, and anticholinergic and antidiarrheal agents. Combining such supportive therapies can be useful in the beginning of a treatment regimen in reducing a patient's symptoms and improving their quality of life. Supportive therapies include administering oral iron, folate, and vitamin $B_{12}$. Antidiarrheal agents include, but are not limited to diphenoxylate, codeine, loperamide, and anticholinergics (or pharmacological equivalents thereof), which can be administered to patients with mild disease to reduce the frequency of bowel movements and relive rectal urgency. Cholestyramine can be used in patients to prevent bile salt-induced colonic secretion in patients who have already undergone limited ileocolic resections. Anticholinergic agents include, but are not limited to, clidinium bromide, dicyclomine hydrochloride, tincture of *belladonna* and the like, and are useful to reduce abdominal cramps, pain and rectal urgency. Supportive or therapies may be administered by routes, and at dosages and intervals, that are known in the art and described in the prescribing information In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the alpha4beta7 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

The following examples, both actual and prophetic, are provided for the purpose of illustrating specific embodiments or features of the instant invention and do not limit its scope.

Example 1

This Example describes various assays used in studying the PK/PD properties of 18A11.

Quantitative Determination of Drug

This example describes an assay used to measure the amount of 18A11 in serum from a subject. Briefly, capture antibody (for example, mouse anti-18A11 1.30.1mAb) is passively adsorbed to Multi-Array® 96-well HighBind microplate wells (Meso Scale Discovery). The microplate wells are blocked with Blocker™ BLOTTO/Tween buffer after removing excess capture antibody. Standards and quality control samples, prepared by spiking known quantities of 18A11 into 100% normal human serum pool are loaded into the microplate wells after pre-treating with a dilution factor of 50 in Blocker™ BLOTTO/Tween buffer, as are samples to be tested and matrix blank. Any 18A11 in the samples is captured by the immobilized capture antibody. Unbound material is removed by washing the microplate wells. Following washing, SULFO-TAG™ conjugated detection antibody (for example, anti-18A11 1.2.1 mAb) is added to the microplate wells to bind captured 18A11. Unbound SULFO-TAG™ conjugated capture antibody is removed by washing the microplate wells.

Following this washing, Read Buffer T (Meso Scale Discovery) is added to aid in the detection of bound SULFO-TAG™ conjugated detection antibody. When the microplate is electrically stimulated, the SULFO-TAG™ label, in the presence of the co-reactant tripropylamine (TPA) in the read buffer, emits light at 620 nm. The quantity of light emitted is proportional to the amount of 18A11 bound by the capture antibody in the initial step. Light emission is detected using an appropriate plate reader; for example, a Sector Imager 6000 equipped with Discovery Workbench software. Data are reduced, for example, using Watson Laboratory Information Management System data reduction package using a 5PL (autoestimate) (5-parameter logistic) regression model with a weighting factor of 1/Y2. The amount of 18A11 in a given serum sample is determined by comparison to the standard curve formed by the standards and quality control samples.

Anti-18A11 Binding Antibody Immunoassay

This example describes an assay used to detect the presence of antibodies that bind 18A11 in serum from a subject. The detection of binding antibodies to 18A11 in this assay utilizes electrochemiluminescence (ECL) MSD (Meso Scale Discovery) technology platform, and is based on multivalent characteristics of antibody binding. The testing strategy involves a tiered two-assay approach consisting of a screening assay and a specificity assay. Samples with signal to noise ratio (S/N) greater than assay cut point in the screening assay are further tested in the specificity assay by incubating the sample with excess 18A11 prior to testing.

To enable dissociation of antibody complexes, acid treatment of samples is performed prior to analysis. Acid-treated serum samples and controls are added to a solution consisting of equal parts of biotinylated-18A11 (B-18A11) and ruthenylated-18A11 (Ru-18A11) in 1 M Tris, pH 9.5, and are incubated at ambient temperature to allow for anti-18A11 antibodies to bind both a B-18A11 molecule and a Ru-18A11 molecule, thereby forming a complex.

Following the incubation, all samples and controls are transferred to a washed streptavidin-coated standard bind MSD plate blocked with bovine serum albumin and incubated at ambient temperature to allow for the capture of B-18A11 and formed complexes on the streptavidin surface. The plate wells are washed and a solution of MSD read buffer containing tripropylamine is added. The plate is read on the MSD Sector Imager 6000 plate reader. Within the instrument, ruthenium participates in an electrochemiluminescent reaction that is triggered when the voltage was applied. The complexes containing the Ru-18A11 that are captured on the wells of the plate result in an ECL signal proportionate to the concentration of anti-18A11 antibodies in the sample.

Anti-18A11 Neutralizing Antibody Bioassay

This example describes an assay used to detect the presence of antibodies that neutralize 18A11 in serum from a subject. The anti-18A11 neutralizing antibody (NAb) testing strategy involves a tiered two-assay approach consisting of a screening assay and a specificity assay. The purpose of the screening assay is to detect any inhibition to 18A11 activity in test serum samples. The specificity assay is conducted by incubating sample with excess 18A11 prior to analysis to confirm that the inhibition of 18A11 activity observed in the screening assay was specific to the presence of neutralizing anti-18A11 antibodies. The combined results of the screening and specificity assays are used to determine if a sample is positive or negative for anti-18A11 neutralizing antibodies.

In this assay, Chinese Hamster Ovary (CHO) cells stably transfected with human alpha4beta7 integrin expressed on the cell surface (CHO-alpha4beta7) are incubated in the presence of a fixed concentration of human biotin-labeled soluble form of MadCAM-1 (Bi-MadCAM-1FC) and 18A11. 18A11 binds to alpha4beta7 expressed on the surface of CHOalpha4beta7 cells and blocks Bi-MadCAM-1FC binding to alpha4beta7. If anti-18A11 neutralizing antibodies are present in the sample, 18A11 binding to alpha4beta7 is impaired as detected by the increase of the fluorescent signal of phycoerythrin conjugated streptavidin (SA-PE) measured by using a 96-well plate fluorescence reader as relative fluorescence units (RFU).

Immunophenotyping and Receptor Occupancy

This example describes a six-color, six tube flow cytometry assay IPRO (immunophenotyping and receptor occupancy) assay to assess receptor occupancy and enumerate CD4 T cell subsets in human subjects. Both free and total levels of alpha4beta7 receptor are assayed in separate tubes, using the tube format shown in Table 3 below. The ability to identify both free and total levels of alpha4beta7 is accomplished by using two reagents, an antibody that competes with 18A11 for binding to alpha4beta7 (referred to as 'competing a4b7' in Table 3 below), and an antibody that binds the beta7 subunit of alpha4beta7 and does not compete with 18A11 (referred to as 'non-com. b7' in Table 3 below), each of which are conjugated to phycoerythrin. The reagents also include anti-CD103 (alphaE), which is used to exclude cells expressing alphEbeta7 (which will bind the non-com. b7 antibody) from the analysis. The addition of an approximately 500 microgram/ml 18A11 ex vivo drug spike condition serves as full-saturation control. High quality custom flow cytometry reagents include 1:1 antibody-fluorophore conjugates, antibody cocktails and lyophilized drug and placebo buffer (lyo buffer, in Table 3 below).

TABLE 3

Six Tube IPRO Assay

| Tube | Purpose | FITC | PE | PerCP | Alexa Fluor ® 647 | APC-H7 | V450 |
|---|---|---|---|---|---|---|---|
| 1 | RO (free) (Iyo buffer) | CD8 + CD103 | Competing a4b7 | CD45 | CCR7 | CD45 RA | CD3 |
| 2 | 18A11 pre-incubation ex-vivo-establishes floor of RO assay | CD8 + CD103 | Competing a4b7 | CD45 | CCR7 | CD45 RA | CD3 |
| 3 | RO (total) and cell counts (Iyo buffer) | CD8 + CD103 | Non-com. b7 | CD45 | CCR7 | CD45 RA | CD3 |
| 4 | Control for gate placement (Iyo buffer) | CD8 + CD103 | Non-com. b7 | CD45 | | CD45 RA | CD3 |
| 5 | Monitor skin homing vs. gut homing (Iyo buffer) | CLA | Non-com. b7 | CD45 | CD4 | CD45 RA | CD3 |
| 6 | Sample quality (TBNK, CD4) (Iyo buffer) | CD19 | CD4 | CD45 | CD16 + CD56 | CD8 | CD3 |

FITC: fluorescein isothiocyanate
PE: phycoerythrin
PerCP: Peridinin-chlorophyll proteins
AlexaFluor ® 647: a synthetic fluorescent dye with an excitation maxima of approximately 647 nm
APC-H7: allophycocyanin an accessory photosynthetic pigment found in bluegreen algae)-cyanine tandem fluorochrome
V450: a coumarin dye excited by the violet laser A set of six tubes is prepared for each subject (or control) to be analyzed. The drug or placebo buffer may be lyophilized and prepared as individual kits. For each assay, each of six tubes (as shown in Table 3) in the kit is rehydrated in 20 microliters of water and incubated for approximately 5 minutes. Alternatively, drug or placebo is placed into each of the six tubes. To each tube there is then added 100 microliters of peripheral blood from the subject to be analyzed. The tubes are then incubated at room temperature for approximately 30 minutes, after which, 20 microliters of antibody cocktail plus 60 microliters of Antibody:PE 1:1 reagents are added to each tube. After an additional incubation at room temperature for approximately 20 minutes, red blood cells are lysed, and the remaining cells are washed, resuspended and analyzed using a fluorescence activated cell sorter. A gating strategy that allows differentiation of lymphocytes and a comparison of subtypes thereof facilitates the identification and differentiation of CD4 effector memory T cells, CD4 central memory T cells and CD4 naïve T cells. To enumerate CD4 T cell subsets a dual-platform approach is employed. For example, the number of CD4 naïve T cell events collected for each population is divided by the lymphocyte events and then multiplied by the hematology result of lymphocytes per microliter. The example following equation is employed, where naïve CD4 T cells are defined as CCR7+ CD45RA+ CD3+ CD8− CD103− CD45+ lymphocytes:

{[CCR7+CD45RA+CD3+CD8−/CD103−CD45+lymphocyte events]/[CD45+/SSC lymphocyte events]}×[LYM_RAW(column BQ)*1000]

The competitive anti-alpha4beta7-PE binds to free (unoccupied) alpha4beta7 target receptor on all analyzed T cell subsets, while the non-competing antibody (non-com b7) binds to both free (unoccupied) and occupied alpha4beta7. A signal corresponding to full target saturation is obtained for each subject/time-point by including an "ex-vivo spike" sample with a saturating concentration of 18A11. The median fluorescence intensity values for spiked and non-spiked conditions are converted to molecules bound per cell (MBPC) using a fluorescent bead standard curve and then utilized to calculate receptor occupancy. The calculation for target saturation is the difference in competitive anti-alpha4beta7-PE signal between spiked and non-spiked samples for a given subject/time-point relative to the average of the subject's predose values. For example, if there are two predose values available for a subject, calculated target saturation uses the following equation:

$$\frac{(MBPC \text{ non-spiked} - MBPC \text{ spiked}) \text{ Post-dose}}{\{(MBPC \text{ non-spiked} - MBPC \text{ spiked})\text{Pre-}d1 + (MBPC \text{ non-spiked} - MBPC \text{ spiked})\text{Pre-}d2\}/2}$$

It is understood by those of skill in the art the term "tube" is used herein for convenience; any suitable container could be employed, including microwell plates, cuvettes and the like. It is also understood that the reagent tubes can be prepared before a sample is obtained, and dehydrated, with re-hydration occurring shortly before the sample is added. Alternatively, the reagent tubes can be prepared after a sample is obtained, or at the same time a sample is obtained.

Example 2

This example describes a Phase 1, randomized, double-blind, placebo-controlled, ascending single dose study to evaluate the safety, tolerability, pharmacokinetics (PK) and pharmacodynamics (PD) of 18A11 in healthy subjects (HS) and subjects with mild to moderate ulcerative colitis (UC; ClinicalTrials.gov Identifier: NCT01164904). The following doses are evaluated:

proportional across the 21- to 210-mg SC dose range. Across the 70- to 420-mg IV dose range, both $C_{max}$ and AUC were dose proportional.

The duration of target coverage was also dose proportional for both the SC and IV routes of administration, with saturation (>99%) of $\alpha_4\beta_7$ receptors on circulating CD4+ T cells achieved for >28 days following single doses of 18A11 21 mg SC and >128 days following single doses of 18A11 210 mg SC or IV. Results are shown in Table 4.

TABLE 4

PK Parameters for Single Dose Study

| Regimen | | $t_{max}$ (day) | $C_{max}$ (microg/mL) | $AUC_{last}$ (day * microg/mL) | $AUC_{inf}$ (day * microg/mL) |
|---|---|---|---|---|---|
| Cohort 1: 0.7 mg SC (N = 1-4) | Mean (SD) | 2 (2-3) | 0.0169 (0.0185) | 0.0325 (0.0568) | 0.161 (—) |
| Cohort 2: 2.1 mg SC (N = 4) | Mean (SD) | 3.5 (2-7) | 0.126 (0.100) | 0.999 (0.947) | 1.28 (0.907) |
| Cohort 3: 7 mg SC (N = 5-6) | Mean (SD) | 4 (2-4) | 0.205 (0.108) | 2.18 (1.55) | 3.06 (1.25) |
| Cohort 4: 21 mg SC (N = 5) | Mean (SD) | 7 (3-10) | 2.51 (0.564) | 62.9 (13.3) | 64.2 (14.1) |
| Cohort 5: 70 mg SC (N = 6) | Mean (SD) | 5.5 (3-10) | 10.1 (2.45) | 374 (151) | 391 (139) |
| Cohort 6: 210 mg SC (N = 6) | Mean (SD) | 10 (7-14) | 29.8 (6.19) | 1670 (464) | 1700 (474) |
| Cohort 7: 70 mg IV (N = 6) | Mean (SD) | 0.0417 (—) | 23.0 (3.50) | 499 (33.4) | 500 (33.4) |
| Cohort 8: 210 mg IV (N = 6) | Mean (SD) | 0.0417 (—) | 72.1 (13.3) | 1740 (272) | 1840 (391) |
| Cohort 9: 420 mg IV (N = 6) | Mean (SD) | 0.0417 (0.0417-4) | 151 (35.3) | 4410 (773) | 4470 (793) |

Abbreviations: $AUC_{inf}$ = area under the concentration-time curve from time 0 to infinity; $AUC_{last}$ = area under the concentration-time curve from time 0 to the last observation post dose; $C_{max}$ = maximum observed concentration; IV = intravenous(ly); SC = subcutaneous(ly); $t_{max}$ = time to maximum observed concentration; "—" = not applicable.
Note:
$t_{max}$ presented as median (range)

| Cohort # | Population | Dose | Route | N (18A11:placebo) |
|---|---|---|---|---|
| 1 | HS | 0.7 mg | SC | 6 (4:2) |
| 2 | HS | 2.1 mg | SC | 6 (4:2) |
| 3 | HS | 7 mg | SC | 8 (6:2) |
| 4 | HS | 21 mg | SC | 8 (6:2) |
| 5 | HS | 70 mg | SC | 8 (6:2) |
| 6 | HS | 210 mg | SC | 8 (6:2) |
| 7 | HS | 70 mg | IV | 8 (6:2) |
| 8 | HS | 210 mg | IV | 8 (6:2) |
| 9 | HS | 420 mg | IV | 8 (6:2) |
| 10 | UC | 210 mg | SC | 8 (6:2) |

Preliminary PK data from healthy subjects from cohorts 1 through 9 were analyzed, and the PK profiles are presented in FIG. 1. Serial blood samples were available for scheduled time points to day 85 for cohorts 1, 2, 3, and 4 (0.7, 2.1, 7, and 21 mg SC 18A11, respectively); and to days 127, 197, 127, 197 and 225 for cohorts 5, 6, 7, 8 and 9 (70 and 210 mg SC 18A11; 70, 210, and 420 mg IV 18A11, respectively). PK and anti-18A11 binding antibody samples were assayed using validated electrochemiluminescent immunoassay (ECL) methods with a lower limit of quantification (LLOQ) of 10 ng/mL and a lower limit of reliable detection (LLRD) of 20 ng/mL, respectively. Nominal times were used for the calculation of PK parameters for this preliminary analysis with results presented in Table 4.

After a single SC injection, 18A11 was quickly absorbed, with mean $C_{max}$ values being reached within 2 to 10 days of dosing, and individual-subject $t_{max}$ values ranging from 2 to 14 days. Compared with 70 and 210 mg IV administrations of 18A11, 70 and 210 mg SC administrations showed mean absolute bioavailabilities of 78% and 92%, respectively. Although 18A11 PK showed nonlinear disposition with the lower doses of 0.7 to 21 mg SC, $C_{max}$ values were dose A two-compartment model with first order absorption and parallel linear and non-linear elimination from the central compartment was found to adequately describe combined serum 18A11 concentration-time data from healthy subjects. Simultaneous PK modeling using all the PK data available yielded a model estimated 18A11 linear elimination half-life of 39 days. Caution should be exercised when using the 39-day half-life to extrapolate 18A11 exposure at the terminal elimination phase when 18A11 concentration in serum drops below 1000 ng/mL, a level at which 18A11 PK may start displaying non-linear target-mediated disposition phase and thus much faster elimination. Results are shown in FIG. 1.

A validated ECL immunoassay method with lower limit of reliable detection (LLRD) of 20 ng/mL was used to test for the presence of anti-18A11 binding antibodies in subject samples. Samples from the healthy subjects enrolled in Study 20090107 in cohorts 1 to 9 (to the end of the study) and from 3 UC subjects in cohort 10 (to days 15, 85 and 127) have been tested, and anti-18A11 binding antibodies have not been detected.

Example 3

Figure 2:
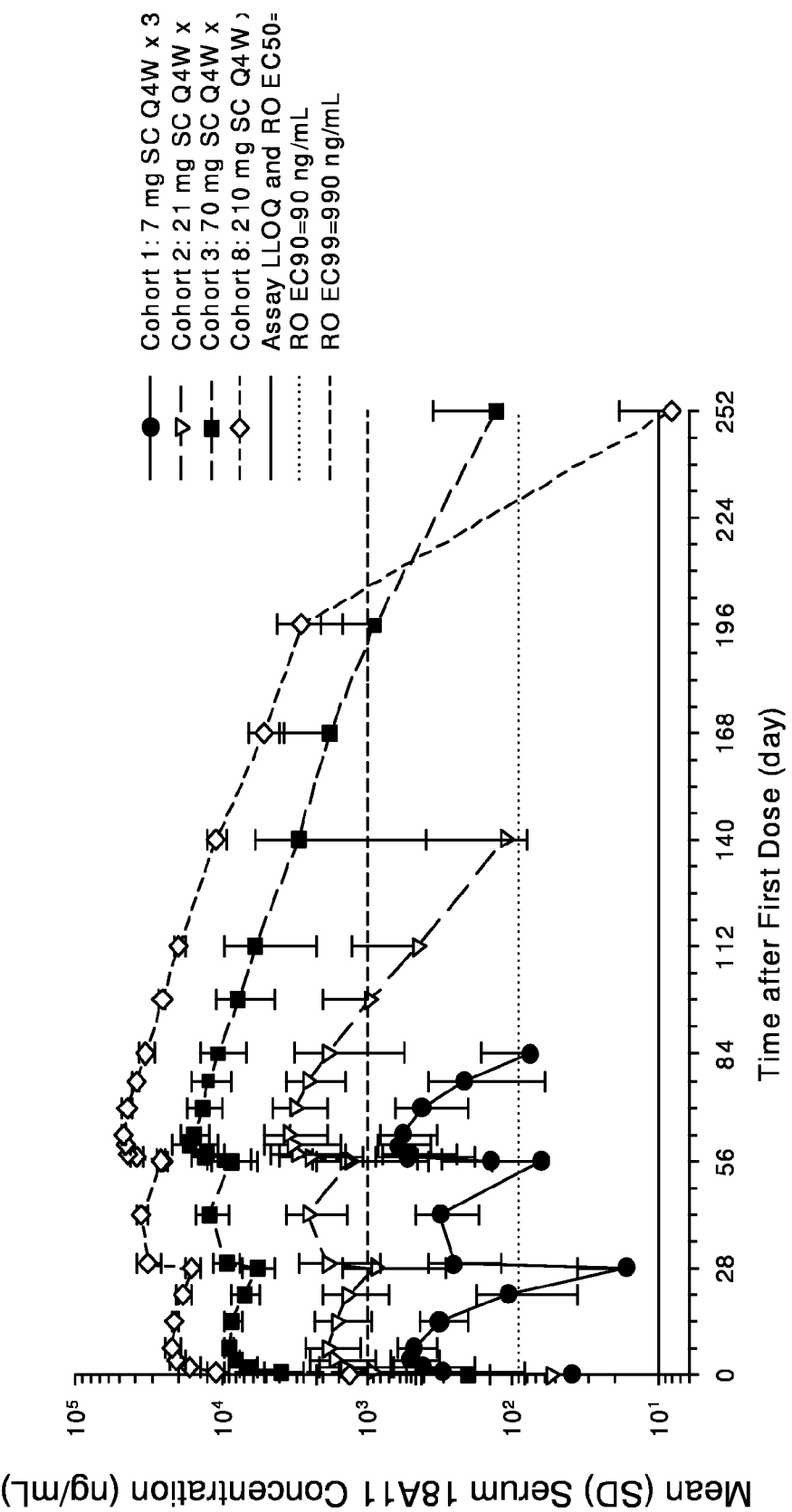
FIG. 2 presents the results of the pharmacokinetic analysis of an ascending multi dose study of 18A11 in healthy subjects (HS). The results shown illustrate the mean (+/−SD) serum 18A11 Concentration-Time Profiles.

This example describes a Phase 1, randomized, double-blind, placebo-controlled, ascending multiple dose study to evaluate the safety, tolerability, pharmacokinetics and pharmacodynamics of 18A11 in healthy subjects and subjects (HS) with mild to moderate ulcerative colitis (UC; ClinicalTrials.gov Identifier: NCT01290042). Preliminary PK data were available for healthy subjects after 3 doses for scheduled time points to days 141, 141, 197, and 85 for cohorts 1, 2, 3 and 8 (7, 21, 70, and 210 mg SC 18A11), respectively. The PK profiles are presented in FIG. 2 and the PK parameters are presented in Table 5.

TABLE 5

PK Parameters for Multi Dose Study

| Regimen | | $t_{max}$ (day) | $C_{max}$ (microg/mL) | $AUC_{tau}$ (day * microg/mL) | $C_{max}$ AR | $AUC_{tau}$ AR |
|---|---|---|---|---|---|---|
| Dose 1 | | | | | | |
| 7 mg SC Q4W × 3 (N = 6) | Mean | 4 | 0.530 | 7.53 | — | — |
| | (SD) | (2-14) | (0.165) | (2.54) | | |
| 21 mg SC Q4W × 3 (N = 7) | Mean | 7 | 2.09 | 43.4 | — | — |
| | (SD) | (7-14) | (0.543) | (16.0) | | |
| 70 mg SC Q4W × 3 (N = 6) | Mean | 7 | 9.19 | 208 | — | — |
| | (SD) | (7-14) | (0.731) | (25.4) | | |
| 210 mg SC Q4W × 3 (N = 7) | Mean | 7 | 24.2 | 577 | — | — |
| | (SD) | (7-14) | (6.16) | (132) | | |
| Dose 3 | | | | | | |
| 7 mg SC Q4W × 3 (N = 6) | Mean | 5.5 | 0.647 | 10.6 | 1.22 | 1.41 |
| | (SD) | (1-7) | (0.266) | (5.14) | | |
| 21 mg SC Q4W × 3 (N = 6) | Mean | 7 | 3.63 | 79.4 | 1.74 | 1.83 |
| | (SD) | (4-14) | (1.65) | (37.3) | | |
| 70 mg SC Q4W × 3 (N = 6) | Mean | 7 | 17.8 | 376 | 1.94 | 1.81 |
| | (SD) | (4-7) | (4.88) | (101) | | |
| 210 mg SC Q4W × 3 (N = 5) | Mean | 7 | 48.3 | 1170 | 2.00 | 2.03 |
| | (SD) | (4-14) | (1.48) | (42.8) | | |

Abbreviations:
AR = dose 3 to dose 1 accumulation ratio;
$AUC_{tau}$ = area under the concentration-time curve within each dosing interval post the reference dose;
$C_{max}$ = maximum observed concentration;
Q4W = once every 4 weeks (monthly);
SC = subcutaneous(ly);
$t_{max}$ = time to maximum observed concentration;
"—" = not applicable.
Note:
$t_{max}$ presented as median (range)

After monthly 7-mg SC dosing for 3 months, approximately 1.22-fold accumulation of 18A11 $C_{max}$ and 1.41-fold accumulation of 18A11 AUC from dose 1 to dose 3 were observed. The corresponding accumulation ratios were 1.74 and 1.83 for the 21-mg SC dosing, 1.94 and 1.81 for the 70-mg SC dosing, and 2.00 and 2.03 for the 210-mg SC dosing. The 28-day mean PK profiles of 18A11 after the first 21 to 210 mg SC doses were comparable with those observed in Study 20090107.

Target occupancy of $\alpha_4\beta_7$ receptors on peripheral blood CD4+ T cells was maintained at >90% for >98 days in response to monthly dosing (×3) of 18A11 at 21 mg SC, 70 mg SC, or 210 mg SC; target occupancy was maintained at 70% to 90% for 84 days in response to monthly dosing (×3) of 18A11 at 7 mg (cohort 1).

A validated ECL immunoassay method with LLRD of 20 ng/mL was used to test for the presence of anti-18A11 binding antibodies in subject samples. As of 13 Dec. 2011, samples from the healthy subjects enrolled in Study 20101261 (to day 141 for cohorts 1 and 2, day 85 for cohort 3, and day 57 for cohort 8) have been tested, and anti-18A11 binding antibodies had not been detected.

Example 4

This example describes a pharmcodynamic analysis for the previously described studies. For the single-dose study, interim 18A11 $\alpha_4\beta_7$ receptor occupancy data were available for healthy subjects: to day 85 for cohorts 1 to 4 (0.7, 2.1, 7, and 21 mg SC), day 127 for cohorts 5 and 6 (70 and 210 mg SC), day 197 for cohorts 7 and 8 (70 and 210 mg IV), and day 225 for cohort 9 (420 mg IV).

Figure 3:
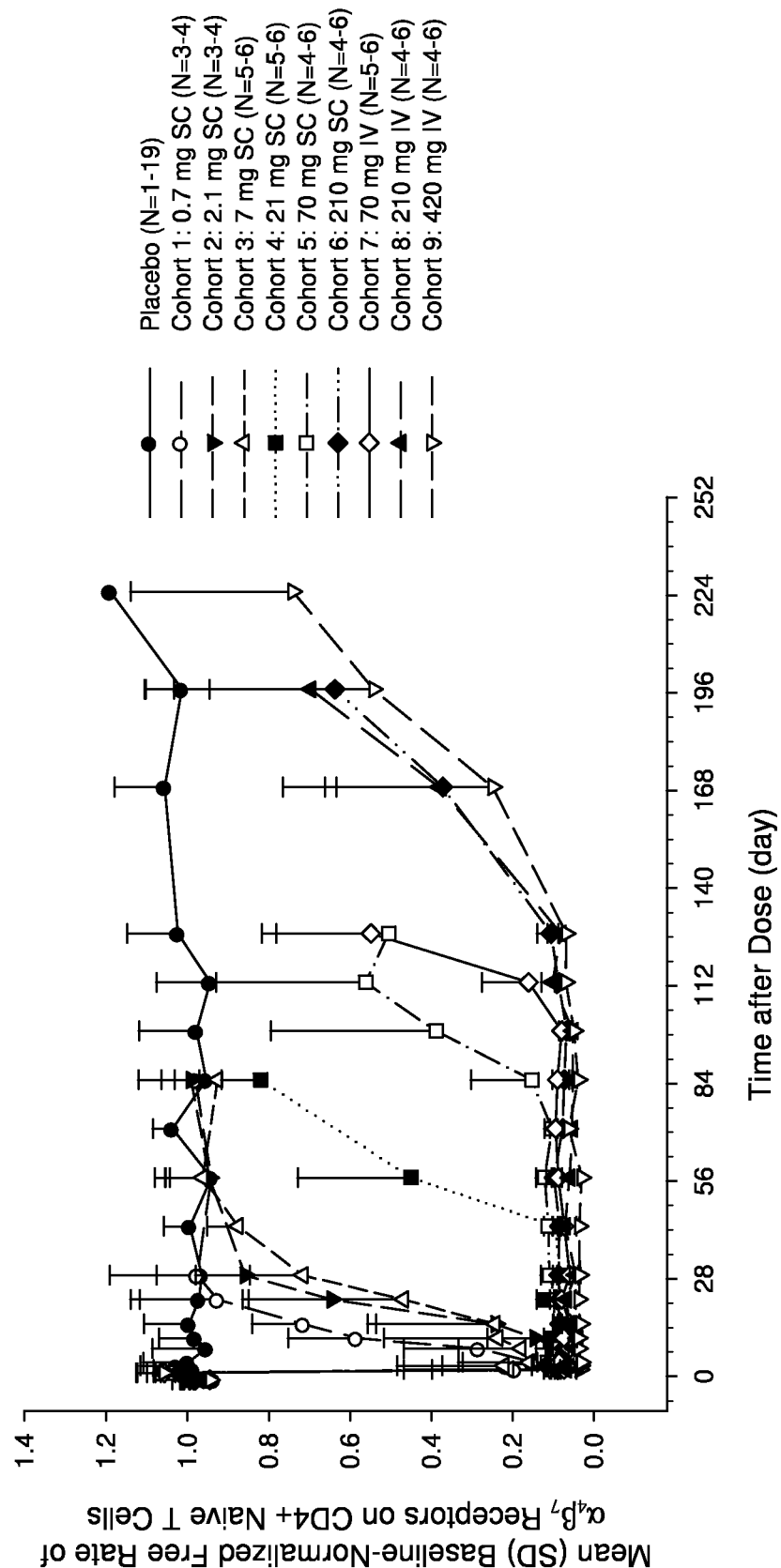
FIG. 3 presents the baseline-normalized free rate of $\alpha_4\beta_7$ receptors on CD4+ Naïve T Cells (Placebo or 18A11), as discussed in Example 4.

The $\alpha_4\beta_7$ receptor occupancy data for cohorts 1 to 9 (healthy subjects) in the single dose study are summarized in FIG. 3. The data demonstrate a dose-proportional and reversible coverage of $\alpha_4\beta_7$ on circulating naïve CD4+ T cells. A similar dose-response profile was observed for memory CD4+ T cell subsets. Total $\alpha_4\beta_7$ levels were found to be reversibly decreased by ~50% upon exposure to saturating doses of 18A11. No significant changes have been observed to date in the absolute counts of CD4+ total, naïve, or memory T cells in these subjects.

Figure 4:
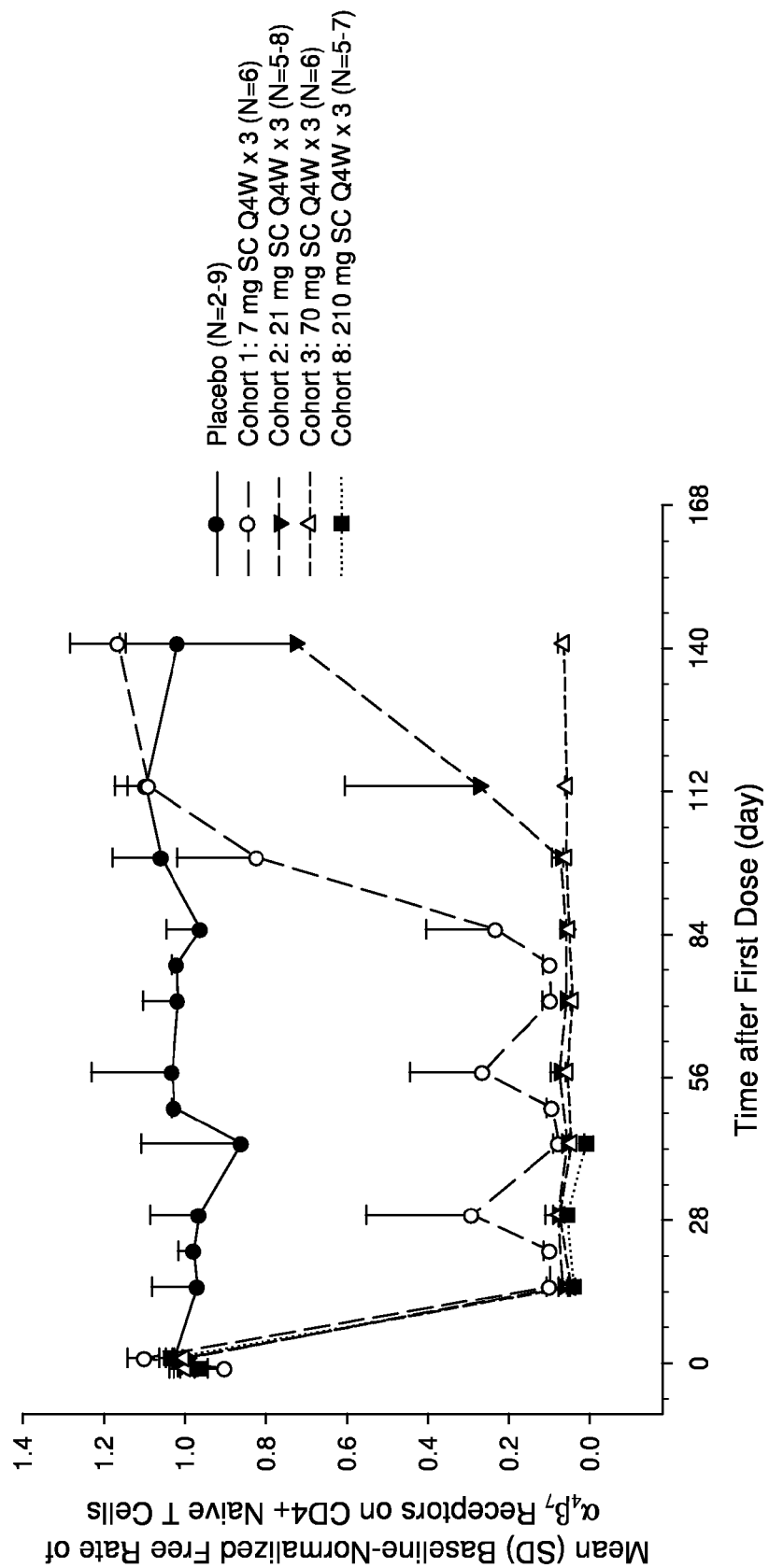
FIG. 4 presents the $\alpha_4\beta_7$ receptor occupancy data summarized for cohorts 1 to 3 and 8 (healthy subjects) in the multi-dose study, as discussed in Example 4.

FIG. 4 presents the $\alpha_4\beta_7$ receptor occupancy data summarized for cohorts 1 to 3 and 8 (healthy subjects) in the multi-dose study. As for the ascending-single dose Study, the data demonstrate a reversible and dose-proportional coverage of $\alpha_4\beta_7$ on circulating naïve CD4+ T cells. A similar dose-response profile was observed for memory CD4+ T cell subsets, and no significant changes have been observed to date in the absolute counts of CD4+ total, naïve, or memory T cells.

Example 5

This example describes clinical observations in patients, and summarizes additional results obtained in two Phase 1, randomized, double-blind, placebo-controlled, study of 18A11 in ulcerative colitis (UC) subjects. Subjects (patients) with ulcerative colitis (UC) were/are treated with a single 210 mg (Study 20090107) or three monthly 21 mg (20101261) subcutaneous (SC) doses of 18A11 (NIH clinical trials website, at the URL "clinicaltrials.gov;" study identifiers NCT01164904 (http://clinicaltrials.gov/ct2/show/NCT01164904) and NCT01290042 (http://clinicaltrials.gov/ct2/show/NCT01290042) for studies 20090107 and 20101261, respectively).

UC subjects diagnosed with active, mild to moderate disease with Mayo score of 4 to 10 (inclusive), and a minimum recto-sigmoidoscopy score of 1 were enrolled. In one cohort (NCT01164904), eight UC subjects were to receive a single dose of 210 mg 18A11 or placebo SC (6:2 ratio), with currently four Caucasian subjects (male:female 2:2; 32-43 yr, 57-77 kg) dosed. In another cohort (NCT01290042), four Caucasian UC subjects (male:female 3:1; 26-51 yr, 73-92 kg) received 21 mg 18A11 or placebo SC (3:1 ratio) monthly for 3 months. Based on 18A11 PK linear elimination phase half-life, predicted alpha4beta7 receptor occupancy (RO), and safety monitoring requirements, subjects were/are to be followed up for 5 and 7 months under the 21 and 210 mg regimens, respectively.

Figure 5A:
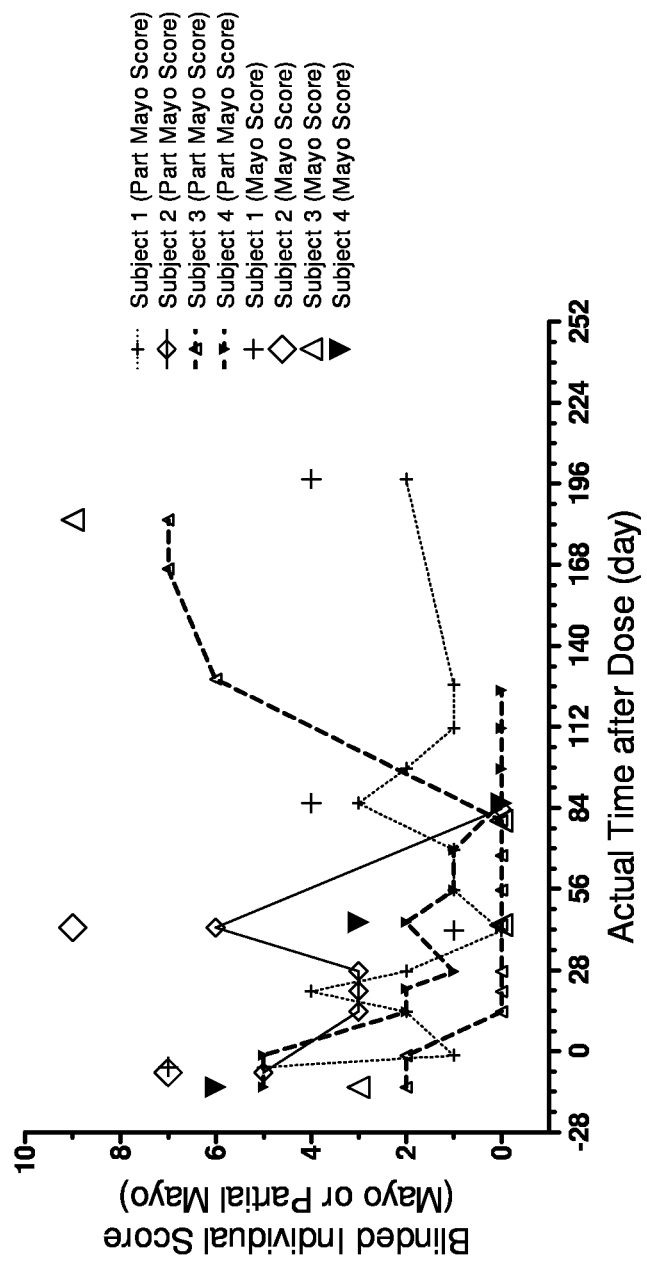
FIG. 5 presents blinded individual Mayo and partial Mayo score profiles observed in patients treated with a single 210 mg dose of 18A11 or placebo (FIG. 5A) or 21 mg of 18A11 or placebo administered every four weeks for a total of three doses (FIG. 5B), as described in Example 5.
Figure 5B:
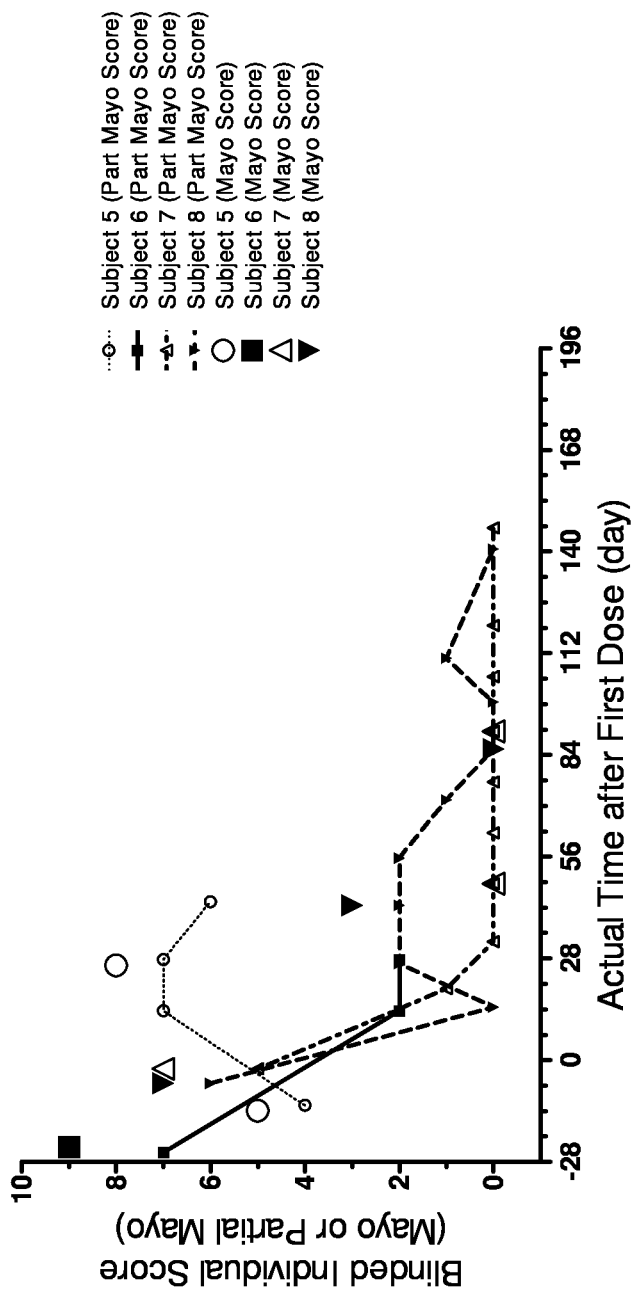

PK, anti-drug antibodies (ADA), safety, PD including RO, CD4+ central memory T cell counts (Tcm), serum high sensitivity C-reactive protein (hsCRP; determined substantially as described by Maharshak et al *J Dig Dis* 9: 140; 2008, using the high sensitivity C-reactive protein (hs-CRP) method) and fecal calprotectin (FC; substantially as described by Vieira et al *BMC Research Notes* 2:221; 2009) biomarkers, and partial Mayo score were measured. Full Mayo score with recto-sigmoidoscopy was assessed during screening, and Weeks 6, 12, and 28 (210 mg only) visits. For the purpose of this analysis, "Remission" is defined as a Mayo Score less than or equal to two, with no individual subscore greater than one point. "Response" is defined as a decrease in Mayo Score from baseline of greater than or equal to three and greater than or equal to 30% plus a decrease in rectal bleeding score of at least one point or absolute reading of 0 or 1. "Mucosal healing" is defined as a rectosigmoidoscopy score of 0 or 1. Results are shown in FIGS. 5A and 5B for the 210 mg and 21 mg cohorts, respectively.

Preliminary assessments of the eight UC subjects' data (median screening Mayo score=7; at least one on placebo) showed that 18A11 PK profiles were generally contained within those from the healthy subjects under the same dosing regimens with no detectible ADA. PK and RO profiles were directly correlated, with ~200% elevated Tcm in some subjects. CRP and FC were decreased in some visits/subjects but small sample size and variability precluded definitive assessment. To date, 3 and 4 subjects were in remission at Weeks 6 and 12, respectively; 5, 5, and 1 subjects were in response at Weeks 6, 12, and 28, respectively; and 5 subjects had mucosal healing at both Weeks 6 and 12. Blinded safety data to date have shown no 18A11-related serious adverse events or deaths, except for one early withdrawal due to colitis flare, but was deemed by the investigator to be not treatment related. Abnormalities in ECGs or neurological examinations were not observed.

Example 6

This example describes a randomized, double-blind, placebo-controlled, single-ascending-dose study to evaluate the safety, tolerability, pharmacokinetics (PK) and pharmacodynamics (PD) of 18A11 in healthy Japanese subjects (HJS; study identifier 20110259). A cohort of healthy Caucasian subjects (HCS), matched pair-wise at ±20% according to body weight with their Japanese counterparts, was included as a comparator. Each HJS cohort consisted of at least four first generation Japanese subjects (i.e., four grandparents, biological parents and subject born in Japan), with the remaining HJS being of either first generation, second generation (four grandparents and biological parents born in Japan) or third generation (four grandparents born in Japan). The following doses were evaluated:

| Cohort # | Population | Dose | Route | N (18A11:placebo) |
|---|---|---|---|---|
| 1 | HJS | 21 mg | SC | 8 (3:1) |
| 2 | HJS | 70 mg | SC | 8 (3:1) |
| 3 | HCS | 70 mg | SC | 8 (3:1) |
| 4 | HJS | 210 mg | SC | 8 (3:1) |

Twenty-four male healthy Japanese subjects (HJS; 22-45 yr, 50-81 kg) and 8 male healthy Caucasian subjects (HCS; 20-45 yr, 60-92 kg) were randomized and administered a single SC dose of 18A11 or placebo (6:2 ratio) at 21 (HJS), 70 (HJS and HCS), or 210 mg (HJS) (cohorts 1 to 4). To date, serial blood samples were available for scheduled time points to days 85, 43, 43, and 14 for cohorts 1, 2, 3, and 4 (21, 70, 70, and 210 mg SC 18A11 or placebo, respectively). PK and anti-18A11 binding antibody samples were assayed using validated electrochemiluminescent immunoassay (ECL) methods with a lower limit of quantification (LLOQ) of 10 ng/mL and a lower limit of reliable detection (LLRD) of 20 ng/mL, respectively. Nominal times were used for the calculation of PK parameters for this preliminary analysis with results presented in Table 6. Blood was collected to assess $\alpha_4\beta_7$ RO and CD4+ T cell counts using a validated whole blood 6-color flow cytometric assay.

Figure 6:
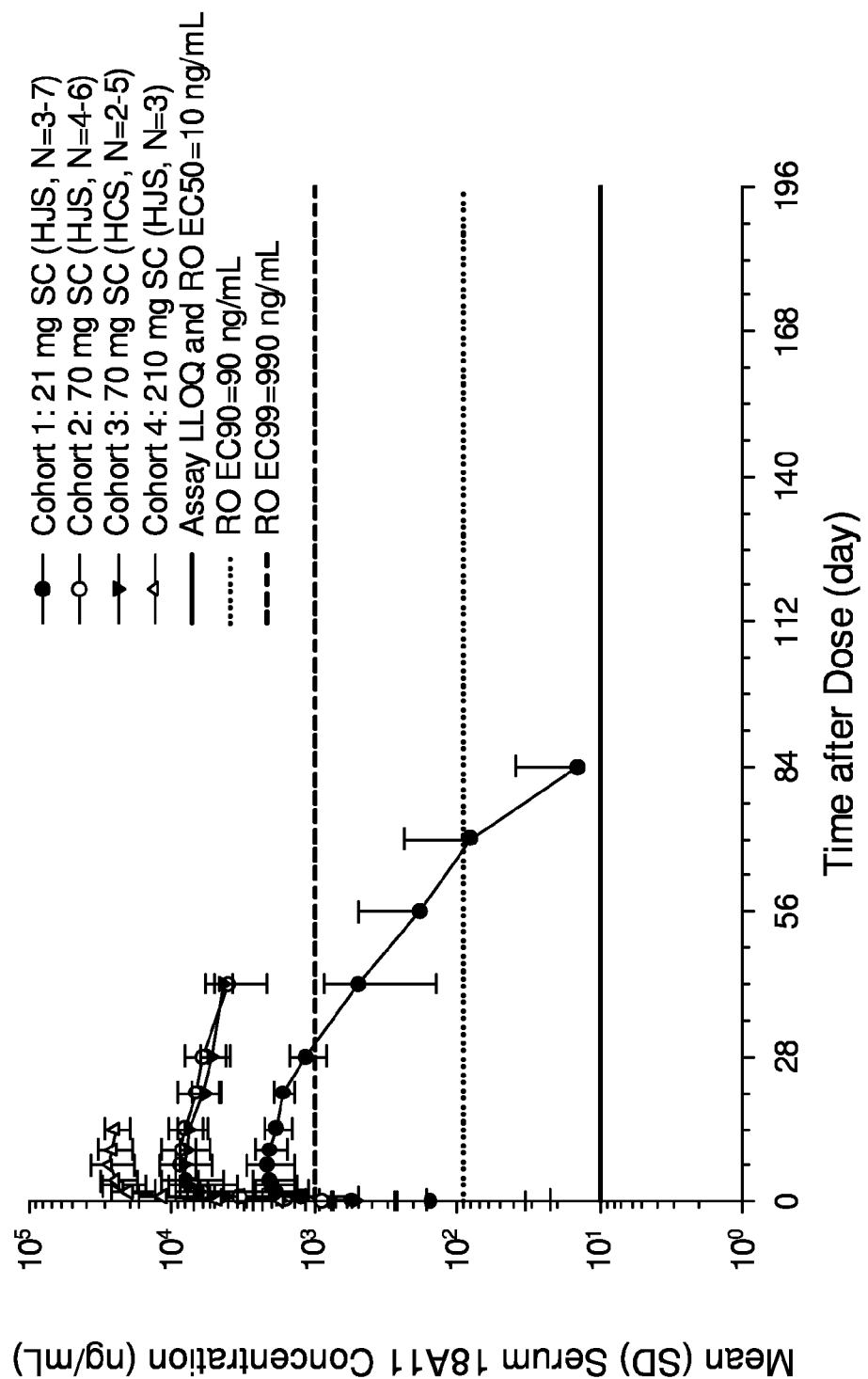
FIG. 6 presents preliminary pharmacokinetic (PK) profiles of 18A11 in healthy Japanese subjects (HJS) and healthy non-Japanese subject (HNJS). The PK profiles were virtually super-imposable between HJS and HNJS under 70 mg SC dosing regimen.
Figure 7:
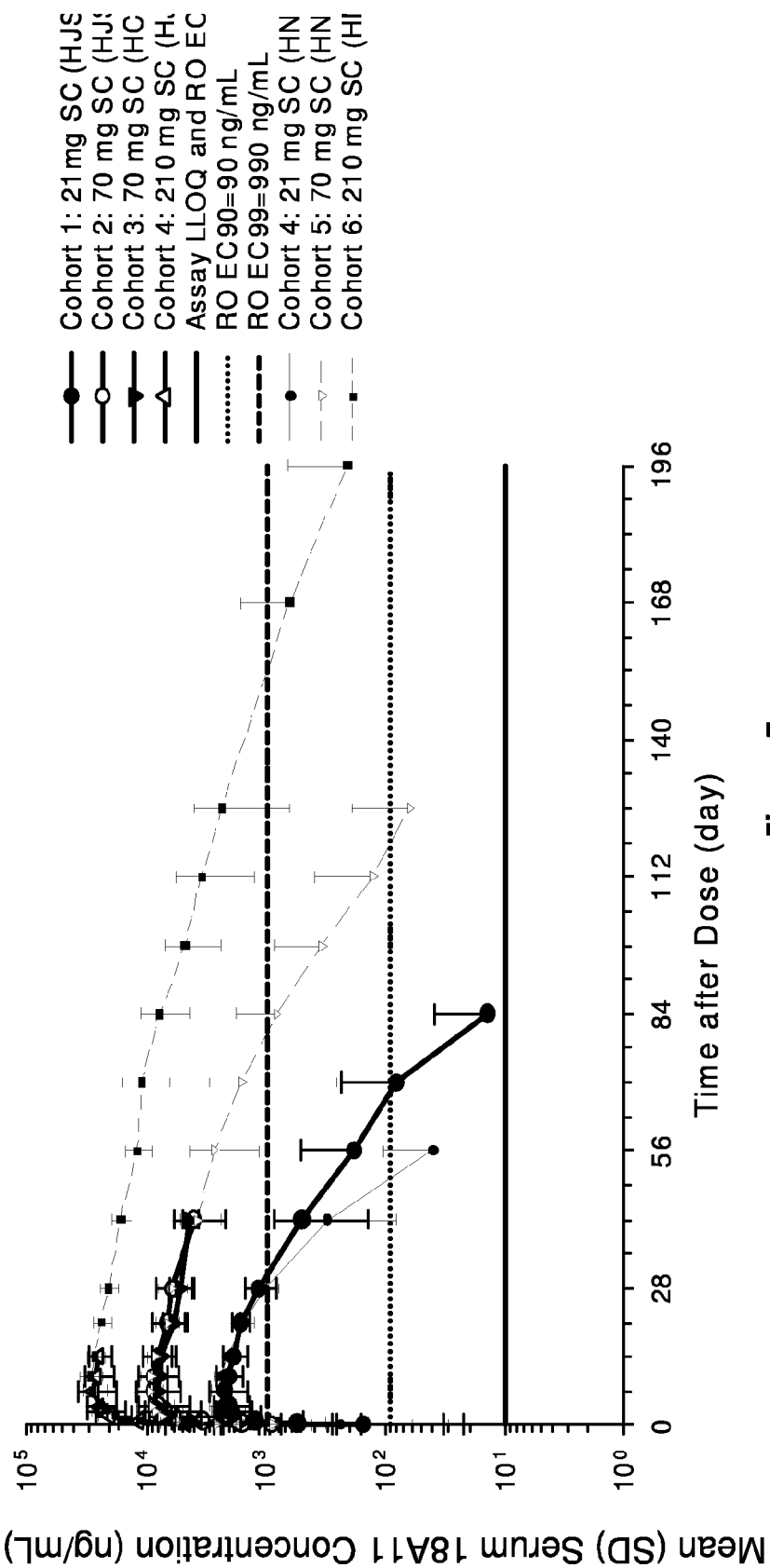
FIG. 7 presents overlaid PK profiles of 18A11 in healthy non-Japanese (HNJS, 14 Caucasian, 7 Black, and 3 Asian; age 20-42 years, weight 65-106 kg from Study 20090107) and HJS and HCS subjects (Study 20110259).
Figure 8:
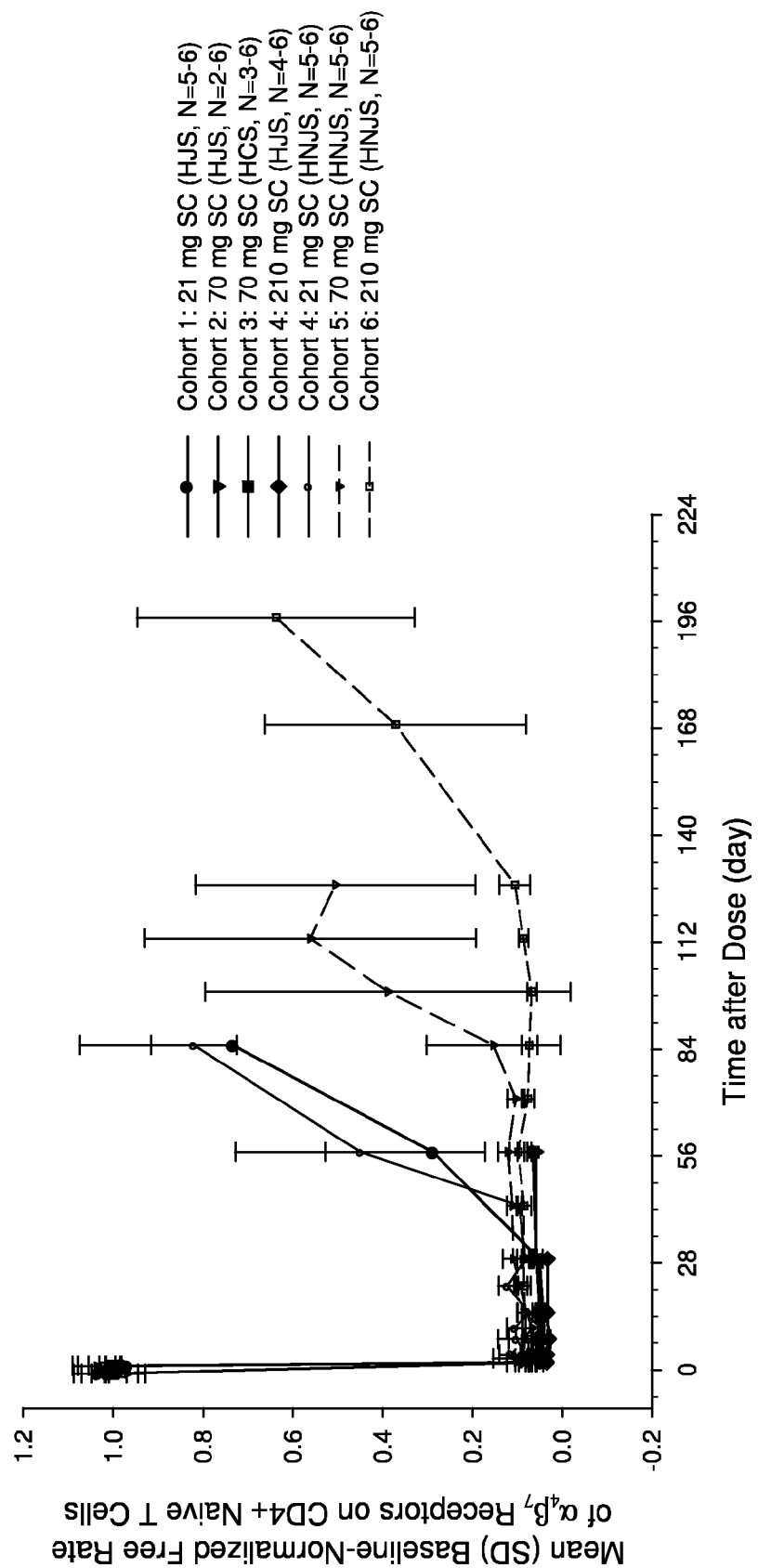
FIG. 8 presents overlaid PD (free $\alpha_4\beta_7$ receptor rate) profiles of 18A11 in healthy non-Japanese (HNJS, 14 Caucasian, 7 Black, and 3 Asian; age 20-42 years, weight 65-106 kg, from Study 20090107) and HJS and HCS subjects (Study 20110259).

Preliminary PK data were analyzed and the PK profiles are presented in FIG. 6, which shows 18A11 PK profiles virtually super-imposable between HJS and HCS under 70 mg SC dosing. FIGS. 7 and 8 present the overlaid PK and PD (free $\alpha_4\beta_7$ receptor rate) profiles of 18A11 in healthy non-Japanese (HNJS, 14 Caucasian, 7 Black, and 3 Asian; age 20-42 years, weight 65-106 kg. Study 20090107) and HJS and HCS subjects (Study 20110259). 18A11 PK/PD profiles are virtually super-imposable between HNJS, HJS and HCS under 70 mg SC dosing, with 21 and 210 mg SC regimens also showing comparable PK/PD profiles between HJS and HNJS. In this study, 18A11 $C_{max}$ was reached within 7 (range: 4 to 14) days of SC dosing. Both 18A11 $C_{max}$ and the estimated $AUC_{(0-4\ weeks)}$ values were dose proportional across the tested 21- to 210-mg range. In addition, 18A11 $C_{max}$ and $AUC_{(0-4\ weeks)}$ estimates under 70 mg SC were similar between HJS and HCS. The $\alpha_4\beta_7$ RO on CD4+ naïve T cells was maintained at >90% for 4, 8, and 4 weeks (data available to date) at 21 mg, 70 mg, and 210 mg SC, respectively. To date, no subjects tested ADA positive at 1 and 3 months after dosing. Blinded safety data to date have shown no 18A11-related serious adverse events or deaths, dose-limiting toxicities, or withdrawals due to adverse events. Abnormalities in ECGs or neurological examinations were not observed.

TABLE 6

PK Parameters for Single Dose Study in Healthy Japanese Subjects

| Regimen | | $t_{max}$ (day) | $C_{max}$ (µg/mL) | $AUC_{(0-4\ weeks)}$ (day * µg/mL) |
|---|---|---|---|---|
| Cohort 1: 21 mg SC (N = 7) | Mean (SD) | 7 (4-14) | 2.27 (0.719) | 47.7 (13.0) |
| Cohort 2: 70 mg SC (N = 6) | Mean (SD) | 7 (4-10) | 8.97 (3.22) | 202 (72.6) |

TABLE 6-continued

PK Parameters for Single Dose Study in Healthy Japanese Subjects

| Regimen | | $t_{max}$ (day) | $C_{max}$ (µg/mL) | $AUC_{(0-4\ weeks)}$ (day * µg/mL) |
|---|---|---|---|---|
| Cohort 3: 70 mg SC (N = 5) | Mean (SD) | 7 (4-10) | 8.47 (1.28) | 188 (32.7) |
| Cohort 4: 210 mg SC (N = 3) | Mean (SD) | 7 (7-14) | 27.8 (9.44) | 632 (131) |

Abbreviations: $AUC_{(0-4\ weeks)}$ = area under the concentration-time curve from time 0 to day 29 (4 weeks) post dose; $C_{max}$ = maximum observed concentration; SC = subcutaneous(ly); $t_{max}$ = time to maximum observed concentration;
Note:
$t_{max}$ presented as median (range)

The 18A11 safety, immunogenicity, and PK/PD properties under single fixed SC dosing regimens are not different among Japanese, Caucasian, and non-Japanese subjects. Japanese subjects with moderate to severe Crohn's disease or ulcerative colitis can be appropriately tested with the dosing regimens implemented in the on-going Phase 2 studies of 18A11 without modifications (Registered at www.clinicaltrials.gov. Study identifiers: NCT01696396 and NCT01694485. Amgen Inc. sponsored on-going Phase 2 studies).

With respect to immunogenicity, all current samples from the healthy subjects (both Caucasian and Japanese) enrolled in the study and from eight UC subjects were tested, and anti-18A11 binding antibodies (ADA) were not detected.

These results support several dosing regimens for administering 18A11 to an individual afflicted with a condition that is associated with inappropriate trafficking of inflammatory gut-homing cells, for example, the trafficking of leukocytes (such as lymphocytes or monocytes) to the gastrointestinal tract or other tissues comprising cells that express MAdCAM-1 (i.e., trafficking to the gut as a result of binding of the leukocytes to the cells that express MAdCAM-1). An appropriate dosing regimen can be selected from the dosing regimens shown in Table 7 below.

TABLE 7

| Dosing Regimens |
|---|
| 7 mg every two weeks (7-21 days); 7 mg includes amounts in the range of 5-14 mg |
| 21 mg every six weeks (14-56 days); 21 mg includes amounts in the range of 15-54 mg |
| 70 mg every 12 weeks (43-126 days); 70 mg includes amounts in the range of 55-149 mg |
| 210 mg every 18 weeks (112-147 days); 210 mg includes amounts in the range of 150-299 mg |
| 420 mg every 6 months (126-224 days); 420 mg includes amounts in the range of 300-1000 mg |

Other dosing regimens are contemplated, and can be determined based on the data presented herein.

What is claimed is:

1. A method of treating a subject afflicted with a condition that is associated with inappropriate trafficking of cells expressing alpha4beta7 to the gastrointestinal tract, wherein the condition is inflammatory bowel disease, comprising administering to the subject an alpha4beta7 heterodimer specific antibody 18A11 in an amount and at an interval selected from the group consisting of:
   (a) 5-14 mg every 7-21 days;
   (b) 15-54 mg every 14-56 days;
   (c) 55-149 mg every 43-126 days;
   (d) 150-299 mg every 112-147 days; and
   (e) 300-1000 mg every 126-224 days;
   wherein 18A11 is an isolated, alpha4beta7 heterodimer-specific antigen binding protein having a heavy chain variable region comprising CDR1, CDR2 and CDR3 from SEQ ID NO:5, and a light chain variable region comprising CDR1, CDR2 and CDR3 from SEQ ID NO:2.

2. The method of claim 1, wherein the amount and interval are selected from the group consisting of:
   (a) 5-10 mg every 11-17 days;
   (b) 15-30 mg every 30-50 days;
   (c) 55-85 mg every 75-95 days;
   (d) 160-260 mg every 120-132 days; and
   (e) 300-700 mg every 165--185 days.

3. The method of claim 1, wherein the amount and interval are selected from the group consisting of:
   (a) 7 mg every 2 weeks;
   (b) 21 mg every 6 weeks;
   (c) 70 mg every 12 weeks;
   (d) 210 mg every 18 weeks; and
   (e) 420 mg every six months.

4. The method of claim 1, wherein 18A11 is an isolated, alpha4beta7 heterodimer-specific antigen binding protein wherein the heavy chain variable region is at least 90% identical to SEQ ID NO:5, and the light chain variable region is at least 90% identical to SEQ ID NO:2.

5. The method of claim 1, wherein 18A11 further comprises a light chain constant region (SEQ ID NO:7) and a heavy chain constant region (SEQ IN NO:8).

6. The method of claim 5, wherein 18A11 differs in amino acid sequence from the amino acid sequences of SEQ ID NO:2 and 5 by the substitution, insertion or deletion of from 1 to 10 amino acids in an 18A 11 variable region.

7. The method of claim 5, wherein 18A11 differs in amino acid sequence from the amino acid sequences of SEQ ID NO:7 and 8 by the substitution, insertion or deletion of from 1 to 10 amino acids in an 18A11 constant region of 18A11.

8. The method of claim 5 wherein the 18A11 incorporate one or more modifications selected from the group consisting of conversion of some, most or substantially all of an N-terminal amino acid to pyroglutamic acid; and removal (either post-translationally or by recombinant technology) of one, two, three, four or five N-terminal and/or C-terminal amino acids.

9. A method of treating a subject afflicted with a condition that is associated with inappropriate trafficking of cells expressing alpha4beta7 to the gastrointestinal tract, wherein the condition is inflammatory bowel disease, comprising administering to the subject an amount of an alpha4beta7 heterodimer specific antibody 18A11 in an amount and at an interval sufficient to achieve and/or maintain a receptor occupancy of at least about 75%; wherein 18A11 is an isolated, alpha4beta7 heterodimer-specific antigen binding protein having a heavy chain variable region comprising CDR1, CDR2 and CDR3 from SEQ ID NO:5, and a light chain variable region comprising CDR1, CDR2 and CDR3 from SEQ ID NO:2.

10. The method of claim 9, wherein the receptor occupancy achieved is at least about 80%.

11. The method of claim 9, wherein the receptor occupancy achieved is at least about 85%.

12. The method of claim 9, wherein the receptor occupancy achieved is at least about 90%.

13. The method of claim 9, wherein the receptor occupancy achieved is at least about 95%.

14. The method of claim 9, wherein the receptor occupancy achieved is at least about 99%.

15. A method of treating a subject afflicted with a condition that is associated with inappropriate trafficking of cells expressing alpha4beta7 to the gastrointestinal tract, wherein the condition is inflammatory bowel disease, comprising administering to the subject an amount of an alpha4beta7 heterodimer specific antibody 18A11 in an amount and at an interval sufficient to achieve and/or maintain a quantity of heterodimer-specific antibody per volume of serum of between 10 ng/ml and 1000 ng/ml; wherein 18A11 is an isolated, alpha4beta7 heterodimer-specific antigen binding protein having a heavy chain variable region comprising CDR1, CDR2 and CDR3 from SEQ ID NO:5, and a light chain variable region comprising CDR1, CDR2 and CDR3 from SEQ ID NO:2.

16. The method of claim 15, wherein the quantity of heterodimer-specific antibody per volume of serum is at least 10 ng/ml.

17. The method of claim 15, wherein the quantity of heterodimer-specific antibody per volume of serum is selected from the group consisting of: at least 25 ng/ml; at least 50 ng/ml; at least 60 ng/ml; at least 70 ng/ml; at least 75 ng/ml; and at least 80 ng/ml.

18. The method of claim 15, wherein the quantity of heterodimer-specific antibody per volume of serum is between 85 ng/ml and 100 ng/ml.

19. The method of claim 15, wherein the quantity of heterodimer-specific antibody per volume of serum is between 70 ng/ml and 150 ng/ml.

20. The method of claim 15, wherein the quantity of heterodimer-specific antibody per volume of serum is between 50 ng/ml and 250 ng/ml.

21. The method of claim 15, wherein the quantity of heterodimer-specific antibody per volume of serum is between 40 ng/ml and 500 ng/ml.

22. The method of claim 15, wherein the quantity of heterodimer-specific antibody per volume of serum is between 25 ng/ml and 750 ng/ml.

23. The method of claim 15, wherein the quantity of heterodimer-specific antibody per volume of serum is between 10 ng/ml and 1,000 ng/ml.

* * * * *